US012558112B2

(12) United States Patent
Thress et al.

(10) Patent No.: US 12,558,112 B2
(45) Date of Patent: Feb. 24, 2026

(54) RECAPTURABLE FUNNEL CATHETERS, AND ASSOCIATED SYSTEMS AND METHODS

(71) Applicant: Inari Medical, Inc., Irvine, CA (US)

(72) Inventors: John Coleman Thress, Capistrano Beach, CA (US); Benjamin Edward Merritt, San Clemente, CA (US); Jacob F. Louw, Carlsbad, CA (US); Jacqueline Macias, Fullerton, CA (US); Brian Michael Strauss, San Clemente, CA (US); Marcus Ian Tambongco Zozulenko, Arleta, CA (US); Christopher Andrew Zikry, Northridge, CA (US); Cheng Lance Ian, Lake Forest, CA (US); Juan Valencia, Fullerton, CA (US)

(73) Assignee: Inari Medical, Inc., Irvine, CA (US)

( * ) Notice: Subject to any disclaimer, the term of this patent is extended or adjusted under 35 U.S.C. 154(b) by 24 days.

(21) Appl. No.: 17/339,663

(22) Filed: Jun. 4, 2021

(65) Prior Publication Data

US 2021/0378694 A1     Dec. 9, 2021

Related U.S. Application Data

(60) Provisional application No. 63/035,605, filed on Jun. 5, 2020.

(51) Int. Cl.
A61B 17/221     (2006.01)
A61B 17/00     (2006.01)

(52) U.S. Cl.
CPC .. A61B 17/221 (2013.01); A61B 2017/00292 (2013.01); A61B 2017/2215 (2013.01)

(58) Field of Classification Search
CPC ........ A61B 17/221; A61B 2017/00292; A61B 2017/2215; A61B 2017/22079;
(Continued)

(56) References Cited

U.S. PATENT DOCUMENTS

| 1,101,890 A | 6/1914 | Tunstead |
| 2,434,835 A | 1/1948 | Colley |
(Continued)

FOREIGN PATENT DOCUMENTS

| AU | 2015210338 | 8/2015 |
| AU | 2016202497 | 5/2016 |
(Continued)

OTHER PUBLICATIONS

US 12,114,876 B2, 10/2024, Quick et al. (withdrawn)
(Continued)

*Primary Examiner* — Katherine H Schwiker
*Assistant Examiner* — Zehra Jaffri
(74) *Attorney, Agent, or Firm* — Perkins Coie LLP

(57)     ABSTRACT

Systems and methods for the intravascular treatment of clot material within a blood vessel of a human patient are disclosed herein. In one embodiment, a funnel catheter assembly includes an outer shaft and an inner shaft extending through and coaxial with the outer shaft. An expandable funnel can be coupled to a distal portion of the inner shaft. The funnel catheter assembly further includes a control assembly operably coupled to the proximal portion of the outer shaft and configured to move the outer shaft between a first position and a second position. In the first position, the outer shaft is positioned at least partially over the funnel to constrain the funnel in a compressed state. In the second position, the outer shaft is retracted proximally relative to the funnel such that the funnel can expand to an expanded state.

14 Claims, 13 Drawing Sheets

(58) Field of Classification Search
CPC ...... A61B 2217/005; A61B 2018/0041; A61B
2017/22035; A61M 25/00; A61F 2/013;
A61F 2/014; A61F 2002/015; A61F 2/01;
A61F 2/0105
See application file for complete search history.

(56) References Cited

U.S. PATENT DOCUMENTS

| | | | |
|---|---|---|---|
| 2,502,639 A | 4/1950 | Blake | |
| 2,695,023 A | 11/1954 | Brown | |
| 2,707,954 A | 5/1955 | Kas, Sr. | |
| 2,784,717 A | 3/1957 | Thompson | |
| 2,846,179 A | 8/1958 | Monckton | |
| 2,955,592 A | 10/1960 | Maclean | |
| 3,088,363 A | 5/1963 | Sparks | |
| 3,197,173 A | 7/1965 | Taubenheim | |
| 3,383,131 A | 5/1968 | Rosfelder | |
| 3,416,531 A | 12/1968 | Edwards | |
| 3,435,826 A | 4/1969 | Fogarty | |
| 3,438,607 A | 4/1969 | Williams et al. | |
| 3,515,137 A | 6/1970 | Santomieri | |
| 3,661,144 A | 5/1972 | Jensen et al. | |
| 3,675,657 A | 7/1972 | Gauthier | |
| 3,785,380 A | 1/1974 | Brumfield | |
| 3,860,006 A | 1/1975 | Patel | |
| 3,863,624 A | 2/1975 | Gram | |
| 3,892,161 A | 7/1975 | Sokol | |
| 3,923,065 A | 12/1975 | Nozick et al. | |
| 4,030,503 A | 6/1977 | Clark, III | |
| 4,034,642 A | 7/1977 | Iannucci et al. | |
| 4,036,232 A | 7/1977 | Genese | |
| 4,187,849 A | 2/1980 | Stim | |
| 4,222,380 A | 9/1980 | Terayama | |
| 4,243,040 A | 1/1981 | Beecher | |
| 4,287,808 A | 9/1981 | Leonard et al. | |
| 4,324,262 A | 4/1982 | Hall | |
| 4,393,872 A | 7/1983 | Reznik et al. | |
| 4,401,107 A | 8/1983 | Harber et al. | |
| 4,469,100 A | 9/1984 | Hardwick | |
| 4,523,738 A | 6/1985 | Raftis et al. | |
| 4,551,862 A | 11/1985 | Haber | |
| 4,604,094 A | 8/1986 | Shook | |
| 4,611,594 A | 9/1986 | Grayhack et al. | |
| 4,634,421 A | 1/1987 | Hegemann | |
| 4,643,184 A | 2/1987 | Mobin-Uddin | |
| 4,646,736 A | 3/1987 | Auth et al. | |
| 4,650,466 A | 3/1987 | Luther | |
| 4,693,257 A | 9/1987 | Markham | |
| 4,705,518 A | 11/1987 | Baker et al. | |
| 4,743,230 A | 5/1988 | Nordquest | |
| 4,776,337 A | 10/1988 | Palmaz | |
| 4,790,812 A | 12/1988 | Hawkins, Jr. et al. | |
| 4,826,483 A | 5/1989 | Molnar, IV | |
| 4,863,440 A | 9/1989 | Chin et al. | |
| 4,870,953 A | 10/1989 | DonMichael et al. | |
| 4,872,579 A | 10/1989 | Palmer | |
| 4,880,408 A | 11/1989 | Cumes et al. | |
| 4,883,458 A | 11/1989 | Shiber | |
| 4,886,062 A | 12/1989 | Wiktor | |
| 4,890,611 A | 1/1990 | Monfort et al. | |
| 4,898,575 A | 2/1990 | Fischell et al. | |
| 4,946,440 A | 8/1990 | Hall | |
| 4,960,259 A | 10/1990 | Sunnanvader et al. | |
| 4,978,341 A | 12/1990 | Niederhauser | |
| 4,981,478 A | 1/1991 | Evard et al. | |
| 5,030,201 A | 7/1991 | Palestrant | |
| 5,053,008 A | 10/1991 | Bajaj | |
| 5,059,178 A | 10/1991 | Ya | |
| 5,064,428 A | 11/1991 | Cope et al. | |
| 5,100,423 A | 3/1992 | Fearnot | |
| 5,127,626 A | 7/1992 | Hilal et al. | |
| 5,129,910 A | 7/1992 | Phan et al. | |
| 5,135,484 A | 8/1992 | Wright | |
| 5,154,724 A | 10/1992 | Andrews | |
| 5,156,594 A | 10/1992 | Keith | |
| 5,158,533 A | 10/1992 | Strauss et al. | |
| 5,158,564 A | 10/1992 | Schnepp-Pesch et al. | |
| 5,192,274 A | 3/1993 | Bierman | |
| 5,192,286 A | 3/1993 | Phan et al. | |
| 5,192,290 A | 3/1993 | Hilal | |
| 5,197,485 A | 3/1993 | Grooters | |
| 5,215,536 A | 6/1993 | Lampropoulos et al. | |
| 5,234,403 A | 8/1993 | Yoda et al. | |
| 5,242,461 A | 9/1993 | Kortenbach et al. | |
| 5,244,619 A | 9/1993 | Burnham | |
| 5,246,011 A | 9/1993 | Caillouette | |
| 5,250,025 A | 10/1993 | Sosnowski et al. | |
| 5,279,546 A | 1/1994 | Mische et al. | |
| 5,323,514 A | 6/1994 | Masuda et al. | |
| 5,329,923 A | 7/1994 | Lundquist | |
| 5,337,780 A | 8/1994 | Kee | |
| 5,360,417 A | 11/1994 | Gravener et al. | |
| 5,364,345 A | 11/1994 | Lowery et al. | |
| 5,370,624 A * | 12/1994 | Edwards ............... | A61M 39/02 |
| | | | 604/110 |
| 5,376,071 A | 12/1994 | Henderson | |
| 5,376,101 A | 12/1994 | Green et al. | |
| 5,378,230 A | 1/1995 | Mahurkar | |
| 5,383,887 A | 1/1995 | Nadal | |
| 5,389,100 A | 2/1995 | Bacich et al. | |
| 5,391,152 A | 2/1995 | Patterson et al. | |
| 5,419,774 A | 5/1995 | Willard et al. | |
| 5,421,824 A | 6/1995 | Clement et al. | |
| 5,429,610 A | 7/1995 | Vaillancourt | |
| 5,443,443 A | 8/1995 | Shiber | |
| 5,456,667 A | 10/1995 | Ham et al. | |
| 5,476,450 A | 12/1995 | Ruggio | |
| 5,484,418 A | 1/1996 | Quiachon et al. | |
| 5,490,859 A | 2/1996 | Mische et al. | |
| 5,496,365 A | 3/1996 | Sgro | |
| 5,527,326 A | 6/1996 | Hermann et al. | |
| 5,549,626 A | 8/1996 | Miller et al. | |
| 5,591,137 A | 1/1997 | Stevens | |
| 5,639,276 A | 6/1997 | Weinstock et al. | |
| 5,653,684 A | 8/1997 | Laptewicz et al. | |
| 5,662,703 A | 9/1997 | Yurek et al. | |
| 5,746,758 A | 5/1998 | Nordgren et al. | |
| 5,749,858 A | 5/1998 | Cramer | |
| 5,769,816 A | 6/1998 | Barbut et al. | |
| 5,782,817 A | 7/1998 | Franzel et al. | |
| 5,800,457 A | 9/1998 | Gelbfish | |
| 5,827,229 A | 10/1998 | Auth et al. | |
| 5,846,251 A | 12/1998 | Hart | |
| 5,860,938 A | 1/1999 | Lafontaine et al. | |
| 5,867,385 A | 2/1999 | Brown et al. | |
| 5,873,866 A | 2/1999 | Kondo et al. | |
| 5,873,882 A | 2/1999 | Straub et al. | |
| 5,876,414 A | 3/1999 | Straub | |
| 5,895,406 A | 4/1999 | Gray et al. | |
| 5,908,435 A | 6/1999 | Samuels | |
| 5,911,710 A | 6/1999 | Barry et al. | |
| 5,911,728 A | 6/1999 | Sepetka et al. | |
| 5,911,733 A | 6/1999 | Parodi | |
| 5,911,754 A | 6/1999 | Kanesaka et al. | |
| 5,941,869 A | 8/1999 | Patterson et al. | |
| 5,947,985 A | 9/1999 | Imram | |
| 5,951,539 A | 9/1999 | Nita et al. | |
| 5,954,737 A | 9/1999 | Lee | |
| 5,971,938 A | 10/1999 | Hart et al. | |
| 5,971,958 A | 10/1999 | Zhang | |
| 5,972,019 A | 10/1999 | Engelson et al. | |
| 5,974,938 A | 11/1999 | Lloyd | |
| 5,989,233 A | 11/1999 | Yoon | |
| 5,993,483 A | 11/1999 | Gianotti | |
| 6,017,335 A | 1/2000 | Burnham | |
| 6,030,397 A | 2/2000 | Moneti et al. | |
| 6,036,717 A | 3/2000 | Mers Kelly | |
| 6,059,745 A | 5/2000 | Gelbfish | |
| 6,059,814 A | 5/2000 | Ladd | |
| 6,066,158 A | 5/2000 | Engelson et al. | |
| 6,068,645 A | 5/2000 | Tu | |
| 6,126,635 A | 10/2000 | Simpson et al. | |
| 6,142,987 A | 11/2000 | Tsugita | |
| 6,146,396 A | 11/2000 | Konya et al. | |

(56) References Cited

U.S. PATENT DOCUMENTS

| | | | |
|---|---|---|---|
| 6,146,403 A | 11/2000 | St. Germain |
| 6,152,144 A | 11/2000 | Lesh et al. |
| 6,152,909 A | 11/2000 | Bagaoisan et al. |
| 6,152,946 A | 11/2000 | Broome et al. |
| 6,156,046 A | 12/2000 | Passafaro et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,809 B1 | 1/2001 | Khairkhahan et al. |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,383,206 B1 | 5/2002 | Gillick |
| 6,398,756 B2 | 6/2002 | Peterson |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,436,085 B1 | 8/2002 | Lauer |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,511,496 B1 | 1/2003 | Huter |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,558,405 B1 | 5/2003 | Mcinnes |
| 6,564,828 B1 | 5/2003 | Ishida |
| 6,569,181 B1 | 5/2003 | Burns |
| 6,575,995 B1 | 6/2003 | Huter et al. |
| 6,575,996 B1 | 6/2003 | Denison |
| 6,589,263 B1 | 7/2003 | Hopkins et al. |
| 6,589,264 B1 | 7/2003 | Barbut et al. |
| 6,592,616 B1 | 7/2003 | Stack |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,220 B1 | 11/2003 | Huter |
| 6,645,222 B1 | 11/2003 | Parodi et al. |
| 6,645,223 B2 | 11/2003 | Boyle |
| 6,652,548 B2 | 11/2003 | Evans et al. |
| 6,656,202 B2 | 12/2003 | Papp |
| 6,656,351 B2 | 12/2003 | Boyle |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,679,893 B1 | 1/2004 | Tran |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,908,455 B2 | 6/2005 | Hajianpour |
| 6,929,652 B1 | 8/2005 | Andrews |
| 6,939,361 B1 | 9/2005 | Kleshinski |
| 6,939,362 B2 | 9/2005 | Boyle |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,004,955 B2 | 2/2006 | Shen |
| 7,004,956 B2 | 2/2006 | Palmer |
| 7,036,707 B2 | 5/2006 | Aota et al. |
| 7,041,084 B2 | 5/2006 | Fotjik |
| 7,048,758 B2 | 5/2006 | Boyle |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,097,651 B2 | 8/2006 | Harrison |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,172,614 B2 | 2/2007 | Boyle |
| 7,179,273 B1 | 2/2007 | Palmer et al. |
| 7,217,255 B2 | 5/2007 | Boyle |
| 7,223,253 B2 | 5/2007 | Hogendijk |
| 7,232,432 B2 | 6/2007 | Fulton, III et al. |
| 7,241,304 B2 | 7/2007 | Boyle |
| 7,244,243 B2 | 7/2007 | Lary |
| 7,252,675 B2 | 8/2007 | Denison |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,973 B2 | 2/2008 | Gesswein |
| 7,331,980 B2 | 2/2008 | Dubrul et al. |
| 7,338,510 B2 | 3/2008 | Boylan |
| 7,344,549 B2 | 3/2008 | Boyle |
| 7,425,215 B2 | 9/2008 | Boyle |
| 7,481,805 B2 | 1/2009 | Magnusson |
| 7,534,234 B2 | 5/2009 | Fotjik |
| 7,544,202 B2 | 6/2009 | Cartier |
| 7,578,830 B2 | 8/2009 | Kusleika et al. |
| 7,621,870 B2 | 11/2009 | Berrada et al. |
| 7,662,166 B2 | 2/2010 | Boyle |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,837,630 B2 | 11/2010 | Nieoson et al. |
| 7,879,065 B2 | 2/2011 | Gesswein |
| 7,905,877 B1 | 3/2011 | Oscar et al. |
| 7,905,896 B2 | 3/2011 | Straub |

(56)  References Cited

U.S. PATENT DOCUMENTS

| | | |
|---|---|---|
| 7,938,809 B2 | 5/2011 | Lampropoulos et al. |
| 7,938,820 B2 | 5/2011 | Webster et al. |
| 7,942,892 B2 | 5/2011 | D'Aquanni et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,275 B2 | 2/2012 | Mialhe |
| 8,118,829 B2 | 2/2012 | Carrison et al. |
| 8,187,465 B2 | 5/2012 | Nierich |
| 8,191,457 B2 | 6/2012 | Kanner et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,262,689 B2 | 9/2012 | Schneiderman |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,366,737 B2 | 2/2013 | Hancock |
| 8,409,215 B2 | 4/2013 | Sepetka et al. |
| 8,439,858 B2 | 5/2013 | Huang et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,496,653 B2 | 7/2013 | Steinke |
| 8,512,352 B2 | 8/2013 | Martin |
| 8,523,897 B2 | 9/2013 | van der Burg et al. |
| 8,529,596 B2 | 9/2013 | Grandfield et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,591,540 B2 | 11/2013 | Boyle |
| 8,608,754 B2 | 12/2013 | Wensel et al. |
| 8,613,717 B2 | 12/2013 | Aklog et al. |
| 8,632,584 B2 | 1/2014 | Henkes et al. |
| 8,641,777 B2 | 2/2014 | Strauss |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,764,730 B2 | 7/2014 | Taber |
| 8,771,289 B2 | 7/2014 | Mohluddin et al. |
| 8,777,893 B2 | 7/2014 | Malewicz |
| 8,777,976 B2 | 7/2014 | Brady |
| 8,784,434 B2 | 7/2014 | Rosenbluth |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,226 B2 | 10/2014 | Gilson et al. |
| 8,882,797 B2 | 11/2014 | Janardhan |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,023,077 B2 | 5/2015 | Cully |
| 9,028,401 B1 | 5/2015 | Bacich et al. |
| 9,044,575 B2 | 6/2015 | Beasley et al. |
| 9,072,537 B2 | 7/2015 | Grandfield et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| D744,639 S | 12/2015 | Aklog et al. |
| 9,204,887 B2 | 12/2015 | Cully et al. |
| 9,216,277 B2 | 12/2015 | Myers |
| 9,241,669 B2 | 1/2016 | Pugh et al. |
| 9,254,352 B2 | 2/2016 | Kumar et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,358,037 B2 | 6/2016 | Farhangnia et al. |
| 9,402,938 B2 | 8/2016 | Aklog et al. |
| 9,439,664 B2 | 9/2016 | Sos |
| 9,439,751 B2 | 9/2016 | White et al. |
| 9,445,828 B2 | 9/2016 | Turjman |
| 9,456,834 B2 | 10/2016 | Folk |
| 9,463,035 B1 | 10/2016 | Greenhalgh et al. |
| 9,463,036 B2 | 10/2016 | Brady et al. |
| 9,492,635 B2 | 11/2016 | Beasley et al. |
| 9,526,864 B2 | 12/2016 | Quick |
| 9,526,865 B2 | 12/2016 | Quick |
| 9,532,792 B2 | 1/2017 | Galdonik et al. |
| 9,545,464 B2 | 1/2017 | Roche et al. |
| 9,566,073 B2 | 2/2017 | Kassab et al. |
| 9,566,179 B2 | 2/2017 | Andreas et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,693,852 B2 | 7/2017 | Lam |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,827,364 B2 | 11/2017 | Peticca et al. |
| 9,844,386 B2 | 12/2017 | Nguyen et al. |

(56)  References Cited

U.S. PATENT DOCUMENTS

| | | | |
|---|---|---|---|
| 9,844,387 | B2 | 12/2017 | Marchand et al. |
| 9,844,643 | B2 | 12/2017 | Beasley et al. |
| 9,848,975 | B2 | 12/2017 | Hauser |
| 9,849,014 | B2 | 12/2017 | Kusleika |
| 9,884,387 | B2 | 2/2018 | Plha |
| 9,931,495 | B2 | 4/2018 | Aboytes |
| 9,937,321 | B2 | 4/2018 | Welch et al. |
| 9,962,178 | B2 | 5/2018 | Greenhalgh et al. |
| 9,980,813 | B2 | 5/2018 | Eller |
| 9,999,493 | B2 | 6/2018 | Nguyen et al. |
| 10,004,531 | B2 | 6/2018 | Rosenbluth et al. |
| 10,010,335 | B2 | 7/2018 | Greenhalgh et al. |
| 10,016,206 | B1 | 7/2018 | Yang |
| 10,016,266 | B2 | 7/2018 | Hauser |
| 10,016,532 | B2 | 7/2018 | Zhang |
| 10,028,759 | B2 | 7/2018 | Wallace et al. |
| 10,045,790 | B2 | 8/2018 | Cox et al. |
| 10,058,339 | B2 | 8/2018 | Galdonik et al. |
| 10,098,651 | B2 | 10/2018 | Marchand et al. |
| 10,117,974 | B2 | 11/2018 | Li |
| 10,130,379 | B2 | 11/2018 | Welch |
| 10,130,385 | B2 | 11/2018 | Farhangnia et al. |
| 10,130,795 | B2 | 11/2018 | Parhangnia et al. |
| 10,179,224 | B2 | 1/2019 | Yang et al. |
| 10,183,147 | B2 | 1/2019 | Yang et al. |
| 10,183,159 | B2 | 1/2019 | Nobles et al. |
| 10,188,829 | B2 | 1/2019 | Beasley et al. |
| 10,195,320 | B2 | 2/2019 | Fisher et al. |
| 10,226,263 | B2 | 3/2019 | Look et al. |
| 10,238,406 | B2 | 3/2019 | Cox et al. |
| 10,271,863 | B2 | 4/2019 | Marks |
| 10,271,864 | B2 | 4/2019 | Greenhalgh et al. |
| 10,327,883 | B2 | 6/2019 | Yachia |
| 10,335,186 | B2 | 7/2019 | Rosenbluth et al. |
| 10,342,571 | B2 | 7/2019 | Marchand et al. |
| 10,349,960 | B2 | 7/2019 | Quick |
| 10,363,054 | B2 | 7/2019 | Vale |
| 10,383,644 | B2 | 8/2019 | Molaei et al. |
| 10,383,983 | B2 | 8/2019 | Aklog et al. |
| 10,384,034 | B2 | 8/2019 | Carrison et al. |
| 10,426,510 | B2 | 10/2019 | Farhangnia et al. |
| 10,426,511 | B2 | 10/2019 | Hehrlein |
| 10,426,644 | B2 | 10/2019 | Shrivastava et al. |
| 10,441,745 | B2 | 10/2019 | Yang et al. |
| 10,448,969 | B2 | 10/2019 | Sutton |
| 10,456,151 | B2 | 10/2019 | Slee et al. |
| 10,456,159 | B2 | 10/2019 | Vetter |
| 10,456,555 | B2 | 10/2019 | Carrison et al. |
| 10,471,234 | B2 | 11/2019 | Taber |
| 10,478,535 | B2 | 11/2019 | Ogle |
| 10,485,952 | B2 | 11/2019 | Carrison et al. |
| 10,492,805 | B2 | 12/2019 | Culbert et al. |
| 10,524,811 | B2 | 1/2020 | Marchand et al. |
| 10,531,883 | B1 | 1/2020 | Deville et al. |
| 10,537,710 | B2 | 1/2020 | Jalgaonkar et al. |
| 10,561,440 | B2 | 2/2020 | Look et al. |
| 10,588,655 | B2 | 3/2020 | Rosenbluth et al. |
| 10,648,268 | B2 | 5/2020 | Jaffrey et al. |
| 10,661,053 | B2 | 5/2020 | Yang et al. |
| 10,695,159 | B2 | 6/2020 | Hauser |
| 10,709,471 | B2 | 7/2020 | Rosenbluth et al. |
| 10,716,880 | B2 | 7/2020 | Culbert et al. |
| 10,729,455 | B2 | 8/2020 | Goyal et al. |
| 10,743,907 | B2 | 8/2020 | Bruzzi et al. |
| 10,772,636 | B2 | 9/2020 | Kassab et al. |
| 10,779,852 | B2 | 9/2020 | Bruzzi et al. |
| 10,779,855 | B2 | 9/2020 | Garrison |
| 10,792,056 | B2 | 10/2020 | Vale et al. |
| 10,799,331 | B2 | 10/2020 | Hauser |
| 10,799,671 | B2 | 10/2020 | Shimada et al. |
| 10,806,559 | B2 | 10/2020 | Bonnette |
| 10,813,663 | B2 | 10/2020 | Bruzzi et al. |
| 10,828,061 | B2 | 11/2020 | Bonnette et al. |
| 10,835,269 | B1 | 11/2020 | Wallace |
| 10,835,271 | B2 | 11/2020 | Ma |
| 10,835,711 | B2 | 11/2020 | Yang et al. |
| 10,874,421 | B2 | 12/2020 | Bruzzi et al. |
| 10,912,577 | B2 | 2/2021 | Marchand et al. |
| 10,926,060 | B2 | 2/2021 | Stern et al. |
| 10,939,932 | B1 | 3/2021 | Yang |
| 10,953,195 | B2 | 3/2021 | Jalgaonkar et al. |
| 10,960,114 | B2 | 3/2021 | Goisis |
| 10,967,111 | B2 | 4/2021 | Iida |
| 10,994,059 | B2 | 5/2021 | Moore |
| 10,994,063 | B2 | 5/2021 | Fisher et al. |
| 11,000,357 | B2 | 5/2021 | Ashkenazi |
| 11,000,682 | B2 | 5/2021 | Merritt et al. |
| 11,013,523 | B2 | 5/2021 | Arad Hadar |
| 11,051,833 | B2 | 7/2021 | Martin et al. |
| 11,058,445 | B2 | 7/2021 | Cox et al. |
| 11,058,451 | B2 | 7/2021 | Marchand et al. |
| 11,065,019 | B1 | 7/2021 | Chou et al. |
| 11,065,028 | B2 | 7/2021 | Parhangnia et al. |
| 11,147,571 | B2 | 10/2021 | Cox et al. |
| 11,147,948 | B2 | 10/2021 | Beasley et al. |
| 11,147,949 | B2 | 10/2021 | Yang et al. |
| 11,154,314 | B2 | 10/2021 | Quick |
| 11,166,703 | B2 | 11/2021 | Kassab et al. |
| 11,185,664 | B2 | 11/2021 | Carrison et al. |
| 11,197,684 | B1 | 12/2021 | Ngo et al. |
| 11,213,356 | B2 | 1/2022 | Tanner et al. |
| 11,224,450 | B2 | 1/2022 | Chou et al. |
| 11,224,721 | B2 | 1/2022 | Carrison et al. |
| 11,253,277 | B2 | 2/2022 | Buck et al. |
| 11,259,821 | B2 | 3/2022 | Buck et al. |
| 11,266,825 | B2 | 3/2022 | Peter et al. |
| 11,278,307 | B2 | 3/2022 | Bruzzi et al. |
| 11,304,713 | B2 | 4/2022 | Hansen |
| 11,305,094 | B2 | 4/2022 | Carrison et al. |
| 11,317,939 | B2 | 5/2022 | Bruzzi et al. |
| 11,337,714 | B2 | 5/2022 | Ferrera et al. |
| 11,376,028 | B1 | 7/2022 | Saadat |
| 11,382,733 | B2 | 7/2022 | Eli |
| 11,383,064 | B2 | 7/2022 | Carrison et al. |
| 11,395,903 | B2 | 7/2022 | Carrison et al. |
| 11,406,418 | B2 | 8/2022 | Bruzzi et al. |
| 11,406,801 | B2 | 8/2022 | Fojtik et al. |
| 11,419,621 | B2 | 8/2022 | Goyal et al. |
| 11,433,218 | B2 | 9/2022 | Quick et al. |
| 11,439,799 | B2 | 9/2022 | Buck et al. |
| 11,457,936 | B2 | 10/2022 | Buck et al. |
| 11,478,262 | B2 | 10/2022 | Ngo et al. |
| 11,510,691 | B2 | 11/2022 | Nguyen et al. |
| 11,529,158 | B2 | 12/2022 | Hauser |
| 11,541,184 | B2 | 1/2023 | Han et al. |
| 11,553,935 | B2 | 1/2023 | Buck et al. |
| 11,553,942 | B2 | 1/2023 | Bonnette et al. |
| 11,554,005 | B2 | 1/2023 | Merritt et al. |
| 11,559,382 | B2 | 1/2023 | Merritt et al. |
| 11,576,691 | B2 | 2/2023 | Chou et al. |
| 11,589,880 | B2 | 2/2023 | Aklog et al. |
| 11,596,768 | B2 | 3/2023 | Stern et al. |
| 11,607,483 | B2 | 3/2023 | Iida |
| 11,633,272 | B2 | 4/2023 | Buck et al. |
| 11,638,637 | B2 | 5/2023 | Buck et al. |
| 11,642,209 | B2 | 5/2023 | Merritt et al. |
| 11,648,028 | B2 | 5/2023 | Rosenbluth et al. |
| 11,672,561 | B2 | 6/2023 | Look et al. |
| 11,678,905 | B2 | 6/2023 | Look et al. |
| 11,697,011 | B2 | 7/2023 | Merritt et al. |
| 11,697,012 | B2 | 7/2023 | Merritt et al. |
| 11,724,052 | B2 | 8/2023 | White et al. |
| 11,730,925 | B2 | 8/2023 | Saadat et al. |
| 11,744,691 | B2 | 9/2023 | Merritt et al. |
| 11,806,033 | B2 | 11/2023 | Marchand et al. |
| 11,819,228 | B2 | 11/2023 | Buck et al. |
| 11,832,837 | B2 | 12/2023 | Hauser |
| 11,832,838 | B2 | 12/2023 | Hauser |
| 11,833,023 | B2 | 12/2023 | Hauser |
| 11,839,393 | B2 | 12/2023 | Hauser |
| 11,839,725 | B2 | 12/2023 | Casey et al. |
| 11,844,921 | B2 | 12/2023 | Merritt et al. |
| 11,849,963 | B2 | 12/2023 | Quick |
| 11,865,291 | B2 | 1/2024 | Merritt et al. |

(56)                    References Cited

U.S. PATENT DOCUMENTS

| | | | | | |
|---|---|---|---|---|---|
| 11,883,043 B2 | 1/2024 | Echarri et al. | 2003/0225379 A1 | 12/2003 | Schaffer et al. |
| 11,890,180 B2 | 2/2024 | Merritt et al. | 2004/0019310 A1 | 1/2004 | Hogendijk |
| 11,918,243 B2 | 3/2024 | Marchand et al. | 2004/0039351 A1 | 2/2004 | Barrett |
| 11,918,244 B2 | 3/2024 | Marchand et al. | 2004/0039412 A1 | 2/2004 | Isshiki et al. |
| 11,925,369 B2 | 3/2024 | Hauser | 2004/0068288 A1 | 4/2004 | Palmer et al. |
| 11,937,834 B2 | 3/2024 | Dinh | 2004/0073243 A1 | 4/2004 | Sepetka et al. |
| 11,937,838 B2 | 3/2024 | Cox et al. | 2004/0098033 A1 | 5/2004 | Leeflang et al. |
| 11,963,861 B2 | 4/2024 | Strauss et al. | 2004/0102807 A1 | 5/2004 | Kusleika et al. |
| 11,969,178 B2 | 4/2024 | Hauser | 2004/0122359 A1 | 6/2004 | Wenz et al. |
| 11,969,331 B2 | 4/2024 | Merritt et al. | 2004/0127936 A1 | 7/2004 | Salahieh et al. |
| 11,969,332 B2 | 4/2024 | Merritt et al. | 2004/0133232 A1 | 7/2004 | Rosenbluth et al. |
| 11,969,333 B2 | 4/2024 | Merritt et al. | 2004/0138525 A1 | 7/2004 | Saadat et al. |
| 11,974,909 B2 | 5/2024 | Merritt et al. | 2004/0138692 A1 | 7/2004 | Phung et al. |
| 11,974,910 B2 | 5/2024 | Merritt et al. | 2004/0167567 A1 | 8/2004 | Cano et al. |
| 11,980,537 B2 | 5/2024 | Merritt et al. | 2004/0199201 A1 | 10/2004 | Kellett et al. |
| 11,986,382 B2 | 5/2024 | Merritt et al. | 2004/0199202 A1 | 10/2004 | Dubrul et al. |
| 11,998,436 B2 | 6/2024 | Merritt et al. | 2004/0260331 A1 | 12/2004 | D'Aquanni et al. |
| 12,016,580 B2 | 6/2024 | Quick et al. | 2004/0260344 A1 | 12/2004 | Lyons et al. |
| 12,023,057 B2 | 7/2024 | Hauser | 2004/0267272 A1 | 12/2004 | Henniges et al. |
| 12,102,343 B2 | 10/2024 | Quick | 2005/0004534 A1 | 1/2005 | Lockwood et al. |
| 12,109,384 B2 | 10/2024 | Merritt et al. | 2005/0033172 A1 | 2/2005 | Dubrul et al. |
| 12,156,669 B2 | 12/2024 | Quick et al. | 2005/0038468 A1 | 2/2005 | Panetta et al. |
| 12,239,333 B2 | 3/2025 | Quick et al. | 2005/0054995 A1 | 3/2005 | Barzell et al. |
| 12,251,120 B2 | 3/2025 | Marchand et al. | 2005/0055047 A1 | 3/2005 | Greenhalgh |
| 12,274,459 B2 | 4/2025 | Dihn | 2005/0080398 A1 | 4/2005 | Markel et al. |
| 12,310,608 B2 | 5/2025 | Marchand et al. | 2005/0085769 A1 | 4/2005 | MacMahon et al. |
| 12,343,028 B2 | 7/2025 | Cox et al. | 2005/0085826 A1 | 4/2005 | Nair et al. |
| 12,364,496 B2 | 7/2025 | Scheinblum et al. | 2005/0085846 A1 | 4/2005 | Carrison et al. |
| 2001/0004699 A1 | 6/2001 | Gittings et al. | 2005/0085849 A1 | 4/2005 | Sepetka et al. |
| 2001/0031981 A1 | 10/2001 | Evans et al. | 2005/0119668 A1 | 6/2005 | Teague et al. |
| 2001/0041881 A1 | 11/2001 | Sarge et al. | 2005/0131387 A1 | 6/2005 | Pursley |
| 2001/0041909 A1 | 11/2001 | Tsugita et al. | 2005/0177132 A1 | 8/2005 | Lentz et al. |
| 2001/0049486 A1 | 12/2001 | Evans et al. | 2005/0187570 A1 | 8/2005 | Nguyen et al. |
| 2001/0049517 A1 | 12/2001 | Zadno-azizi et al. | 2005/0203605 A1 | 9/2005 | Dolan |
| 2001/0051810 A1 | 12/2001 | Dubrul et al. | 2005/0256452 A1 | 11/2005 | DeMarchi et al. |
| 2002/0022858 A1 | 2/2002 | Demond et al. | 2005/0283165 A1 | 12/2005 | Gadberry |
| 2002/0022859 A1 | 2/2002 | Hogendijk | 2005/0283166 A1 | 12/2005 | Greenhalgh et al. |
| 2002/0026211 A1 | 2/2002 | Khosravi et al. | 2005/0283186 A1 | 12/2005 | Berrada et al. |
| 2002/0032455 A1 | 3/2002 | Boock et al. | 2006/0020286 A1 | 1/2006 | Niermann |
| 2002/0049452 A1 | 4/2002 | Kurz et al. | 2006/0042786 A1 | 3/2006 | West |
| 2002/0058910 A1 | 5/2002 | Hermann et al. | 2006/0047286 A1 | 3/2006 | West |
| 2002/0095161 A1 | 7/2002 | Dhindsa | 2006/0074401 A1 | 4/2006 | Ross |
| 2002/0095171 A1 | 7/2002 | Belef | 2006/0079787 A1 | 4/2006 | Whiting et al. |
| 2002/0111648 A1 | 8/2002 | Kusleika et al. | 2006/0085952 A1 | 4/2006 | Kaneko et al. |
| 2002/0120277 A1 | 8/2002 | Hauschild et al. | 2006/0089533 A1 | 4/2006 | Ziegler et al. |
| 2002/0147458 A1 | 10/2002 | Hiblar et al. | 2006/0100662 A1 | 5/2006 | Daniel et al. |
| 2002/0151918 A1 | 10/2002 | Lafontaine et al. | 2006/0142694 A1 | 6/2006 | Bednarek et al. |
| 2002/0156457 A1 | 10/2002 | Fisher | 2006/0149219 A1 | 7/2006 | Calderon |
| 2002/0161392 A1 | 10/2002 | Dubrul | 2006/0155305 A1 | 7/2006 | Freudenthal et al. |
| 2002/0165536 A1 | 11/2002 | Kelley et al. | 2006/0173525 A1 | 8/2006 | Behl et al. |
| 2002/0169474 A1 | 11/2002 | Kusleika | 2006/0195137 A1 | 8/2006 | Sepetka et al. |
| 2002/0173812 A1 | 11/2002 | McGuckin, Jr. et al. | 2006/0200221 A1 | 9/2006 | Malewicz |
| 2002/0173819 A1 | 11/2002 | Leeflang et al. | 2006/0217664 A1 | 9/2006 | Hattler et al. |
| 2002/0188276 A1 | 12/2002 | Evans et al. | 2006/0224177 A1 | 10/2006 | Finitsis |
| 2003/0004536 A1 | 1/2003 | Boylan et al. | 2006/0229645 A1 | 10/2006 | Bonnette et al. |
| 2003/0023263 A1 | 1/2003 | Krolik et al. | 2006/0247500 A1 | 11/2006 | Voegele et al. |
| 2003/0069601 A1 | 4/2003 | Nowakowski et al. | 2006/0253145 A1 | 11/2006 | Lucas |
| 2003/0083693 A1 | 5/2003 | Daniel et al. | 2006/0264905 A1 | 11/2006 | Eskridge et al. |
| 2003/0093106 A1 | 5/2003 | Brady et al. | 2006/0276874 A1 | 12/2006 | Wilson et al. |
| 2003/0100919 A1 | 5/2003 | Hopkins et al. | 2006/0282111 A1 | 12/2006 | Morsi |
| 2003/0114875 A1 | 6/2003 | Sjostrom | 2006/0293696 A1 | 12/2006 | Fahey et al. |
| 2003/0116731 A1 | 6/2003 | Hartley | 2007/0010787 A1 | 1/2007 | Hackett et al. |
| 2003/0125663 A1 | 7/2003 | Coleman et al. | 2007/0038225 A1 | 2/2007 | Osborne |
| 2003/0135151 A1 | 7/2003 | Deng | 2007/0060911 A1 | 3/2007 | Webster et al. |
| 2003/0135230 A1 | 7/2003 | Massey et al. | 2007/0088382 A1 | 4/2007 | Bei |
| 2003/0135258 A1 | 7/2003 | Andreas et al. | 2007/0093744 A1 | 4/2007 | Elmaleh |
| 2003/0144672 A1 | 7/2003 | Gellman et al. | 2007/0112374 A1 | 5/2007 | Paul, Jr. et al. |
| 2003/0153873 A1 | 8/2003 | Luther et al. | 2007/0118165 A1 | 5/2007 | DeMello et al. |
| 2003/0153973 A1 | 8/2003 | Soun et al. | 2007/0149996 A1 | 6/2007 | Coughlin |
| 2003/0168068 A1 | 9/2003 | Poole et al. | 2007/0161963 A1 | 7/2007 | Smalling |
| 2003/0176884 A1 | 9/2003 | Berrada et al. | 2007/0179513 A1 | 8/2007 | Deutsch |
| 2003/0191425 A1 | 10/2003 | Rosenblatt et al. | 2007/0191866 A1 | 8/2007 | Palmer et al. |
| 2003/0191516 A1 | 10/2003 | Weldon et al. | 2007/0198028 A1 | 8/2007 | Miloslavski et al. |
| 2003/0208224 A1 | 11/2003 | Broome | 2007/0208361 A1 | 9/2007 | Okushi et al. |
| 2003/0216774 A1 | 11/2003 | Larson | 2007/0208367 A1 | 9/2007 | Fiorella et al. |
| | | | 2007/0213753 A1 | 9/2007 | Waller |
| | | | 2007/0213765 A1 | 9/2007 | Adams et al. |
| | | | 2007/0233043 A1 | 10/2007 | Dayton et al. |
| | | | 2007/0255252 A1 | 11/2007 | Mehta |

(56) References Cited

U.S. PATENT DOCUMENTS

| 2007/0288054 A1 | 12/2007 | Tanaka et al. |
| 2008/0015541 A1 | 1/2008 | Rosenbluth et al. |
| 2008/0033467 A1 | 2/2008 | Miyamoto et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1* | 9/2008 | Pesce .............. A61B 17/32002 |
| | | 606/171 |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018550 A1 | 1/2009 | Poll |
| 2009/0018566 A1 | 1/2009 | Escudero et al. |
| 2009/0043372 A1 | 2/2009 | Northrop et al. |
| 2009/0054918 A1 | 2/2009 | Henson |
| 2009/0062602 A1 | 3/2009 | Rosenberg et al. |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0082857 A1 | 3/2009 | Lashinski et al. |
| 2009/0160112 A1 | 6/2009 | Ostrovsky |
| 2009/0163846 A1* | 6/2009 | Aklog ................ A61M 1/3621 |
| | | 604/6.11 |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0049225 A1 | 2/2010 | To et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0094320 A1 | 4/2010 | Arat |
| 2010/0106081 A1 | 4/2010 | Brandeis |
| 2010/0114017 A1 | 5/2010 | Lenker et al. |
| 2010/0114113 A1 | 5/2010 | Dubrul |
| 2010/0121312 A1 | 5/2010 | Gielenz et al. |
| 2010/0137846 A1 | 6/2010 | Desai |
| 2010/0190156 A1 | 7/2010 | Van Wordragen et al. |
| 2010/0204712 A1 | 8/2010 | Mallaby |
| 2010/0217261 A1 | 8/2010 | Watson |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0297577 A1 | 11/2010 | Cohen |
| 2010/0318178 A1 | 12/2010 | Rapaport et al. |
| 2010/0331776 A1 | 12/2010 | Salahieh et al. |
| 2011/0009950 A1 | 1/2011 | Grandfield et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0087173 A1 | 4/2011 | Sibbitt, Jr. et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohluddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264132 A1 | 10/2011 | Strauss et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0116440 A1 | 5/2012 | Leynov et al. |
| 2012/0138832 A1 | 6/2012 | Townsend |
| 2012/0143123 A1 | 6/2012 | Agnew |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1 | 5/2013 | Holm et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0172851 A1 | 7/2013 | Shimada et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0046297 A1 | 2/2014 | Shimada et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0135736 A1 | 5/2014 | Hebert |
| 2014/0155830 A1 | 6/2014 | Bonnette et al. |
| 2014/0155908 A1 | 6/2014 | Rosenbluth et al. |
| 2014/0155980 A1 | 6/2014 | Turjman |
| 2014/0163615 A1 | 6/2014 | Gadlage et al. |
| 2014/0180055 A1 | 6/2014 | Glynn et al. |
| 2014/0180397 A1 | 6/2014 | Gerberding et al. |

(56) References Cited

U.S. PATENT DOCUMENTS

| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0276592 A1 | 9/2014 | Mottola et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth et al. |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0119862 A1 | 4/2015 | Cajamarca et al. |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0283309 A1 | 10/2015 | Look et al. |
| 2015/0305756 A1 | 10/2015 | Rosenbluth |
| 2015/0305759 A1 | 10/2015 | St. George et al. |
| 2015/0305859 A1 | 10/2015 | Eller |
| 2015/0314050 A1 | 11/2015 | Beer |
| 2015/0327875 A1 | 11/2015 | Look et al. |
| 2015/0352325 A1 | 12/2015 | Quick |
| 2015/0359547 A1 | 12/2015 | Vale et al. |
| 2015/0360001 A1 | 12/2015 | Quick |
| 2015/0366690 A1 | 12/2015 | Lumauig |
| 2015/0374391 A1 | 12/2015 | Quick |
| 2016/0008014 A1 | 1/2016 | Rosenbluth |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0067450 A1 | 3/2016 | Kowshik |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0128857 A1 | 5/2016 | Kao |
| 2016/0135829 A1 | 5/2016 | Holochwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0220741 A1* | 8/2016 | Garrison ............ A61M 25/0054 |
| 2016/0220795 A1 | 8/2016 | Korkuch et al. |
| 2016/0228134 A1 | 8/2016 | Martin et al. |
| 2016/0250406 A1 | 9/2016 | Parisotto et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0035445 A1 | 2/2017 | Nguyen et al. |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112513 A1 | 4/2017 | Marchand et al. |
| 2017/0112514 A1* | 4/2017 | Marchand ............ A61B 17/221 |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0165468 A1 | 6/2017 | Nobles et al. |
| 2017/0172591 A1 | 6/2017 | Ulm, III |
| 2017/0189041 A1 | 7/2017 | Cox et al. |
| 2017/0196576 A1 | 7/2017 | Long et al. |
| 2017/0203076 A1 | 7/2017 | Groneberg et al. |
| 2017/0209162 A1 | 7/2017 | Sperry et al. |
| 2017/0233908 A1 | 8/2017 | Kroczynski et al. |
| 2017/0238951 A1 | 8/2017 | Yang et al. |
| 2017/0252057 A1 | 9/2017 | Bonnette et al. |
| 2017/0252536 A1 | 9/2017 | Yang et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |
| 2017/0340867 A1* | 11/2017 | Accisano, III ........ A61M 29/00 |
| 2017/0348014 A1 | 12/2017 | Wallace et al. |
| 2018/0014840 A1 | 1/2018 | Panian |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0049873 A1 | 2/2018 | Manash et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0071490 A1 | 3/2018 | Khuu et al. |
| 2018/0078707 A1 | 3/2018 | Loonan |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0235742 A1* | 8/2018 | Fields .................. A61F 2/0105 |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0264230 A1 | 9/2018 | Funk et al. |
| 2018/0280623 A1 | 10/2018 | Pilkington et al. |
| 2018/0289394 A1 | 10/2018 | Shah |
| 2018/0296240 A1 | 10/2018 | Rosenbluth et al. |
| 2018/0296798 A1 | 10/2018 | Kepak et al. |
| 2018/0296801 A1 | 10/2018 | Tegg et al. |
| 2018/0304040 A1 | 10/2018 | Jalgaonkar et al. |
| 2018/0338770 A1 | 11/2018 | Mogi et al. |
| 2018/0339130 A1 | 11/2018 | Ogle |
| 2018/0344339 A1 | 12/2018 | Cox et al. |
| 2018/0344981 A1 | 12/2018 | Laduca et al. |

(56) References Cited

U.S. PATENT DOCUMENTS

| | | | |
|---|---|---|---|
| 2018/0353195 A1 | 12/2018 | Sigmon, Jr. et al. | |
| 2018/0353668 A1 | 12/2018 | Meyer et al. | |
| 2018/0361116 A1 | 12/2018 | Quick et al. | |
| 2019/0000492 A1 | 1/2019 | Casey et al. | |
| 2019/0015298 A1 | 1/2019 | Beatty et al. | |
| 2019/0046219 A1 | 2/2019 | Marchand et al. | |
| 2019/0070401 A1 | 3/2019 | Merritt et al. | |
| 2019/0117244 A1 | 4/2019 | Wallace et al. | |
| 2019/0133622 A1 | 5/2019 | Wallace et al. | |
| 2019/0133623 A1 | 5/2019 | Wallace et al. | |
| 2019/0133624 A1 | 5/2019 | Wallace et al. | |
| 2019/0133625 A1 | 5/2019 | Wallace et al. | |
| 2019/0133626 A1 | 5/2019 | Wallace et al. | |
| 2019/0133627 A1 | 5/2019 | Wallace et al. | |
| 2019/0150959 A1 | 5/2019 | Cox et al. | |
| 2019/0216476 A1 | 7/2019 | Barry et al. | |
| 2019/0223893 A1 | 7/2019 | Gilvarry et al. | |
| 2019/0231372 A1 | 8/2019 | Brady | |
| 2019/0231373 A1 | 8/2019 | Quick | |
| 2019/0239910 A1 | 8/2019 | Brady et al. | |
| 2019/0321071 A1 | 10/2019 | Marchand et al. | |
| 2019/0328411 A1 | 10/2019 | Vale et al. | |
| 2019/0336142 A1 | 11/2019 | Torrie et al. | |
| 2019/0336148 A1 | 11/2019 | Greenhalgh et al. | |
| 2019/0365395 A1* | 12/2019 | Tran | A61L 29/02 |
| 2019/0366036 A1 | 12/2019 | Jalgaonkar et al. | |
| 2019/0366049 A1 | 12/2019 | Hannon et al. | |
| 2019/0374239 A1 | 12/2019 | Martin et al. | |
| 2020/0009301 A1* | 1/2020 | Yee | A61M 1/84 |
| 2020/0022711 A1* | 1/2020 | Look | A61M 1/815 |
| 2020/0030579 A1 | 1/2020 | Taber | |
| 2020/0046368 A1 | 2/2020 | Merritt et al. | |
| 2020/0046940 A1 | 2/2020 | Carrison et al. | |
| 2020/0054861 A1 | 2/2020 | Korkuch et al. | |
| 2020/0060802 A1* | 2/2020 | Hamill | A61M 39/06 |
| 2020/0069889 A1 | 3/2020 | Lin | |
| 2020/0078029 A1* | 3/2020 | Hansen | A61B 17/320758 |
| 2020/0113412 A1 | 4/2020 | Jensen | |
| 2020/0121334 A1 | 4/2020 | Galdonik et al. | |
| 2020/0129741 A1 | 4/2020 | Kawwas et al. | |
| 2020/0155293 A1 | 5/2020 | Morrison et al. | |
| 2020/0187596 A1 | 6/2020 | Krout et al. | |
| 2020/0222666 A1 | 7/2020 | Chan et al. | |
| 2020/0246029 A1 | 8/2020 | Singleton | |
| 2020/0297376 A1 | 9/2020 | Marks | |
| 2020/0324079 A1 | 10/2020 | Jalgaonkar et al. | |
| 2020/0375616 A1 | 12/2020 | Fitz | |
| 2020/0397452 A1 | 12/2020 | Twomey | |
| 2021/0022843 A1 | 1/2021 | Hauser | |
| 2021/0038385 A1 | 2/2021 | Popp et al. | |
| 2021/0069468 A1 | 3/2021 | Keating et al. | |
| 2021/0113224 A1 | 4/2021 | Dinh | |
| 2021/0128182 A1 | 5/2021 | Teigen et al. | |
| 2021/0128184 A1 | 5/2021 | Fulkerson et al. | |
| 2021/0128185 A1 | 5/2021 | Nguyen et al. | |
| 2021/0128893 A1 | 5/2021 | Twomey et al. | |
| 2021/0137667 A1 | 5/2021 | Sonnette et al. | |
| 2021/0138193 A1 | 5/2021 | Garrison et al. | |
| 2021/0138194 A1 | 5/2021 | Carrison et al. | |
| 2021/0153884 A1 | 5/2021 | Casey | |
| 2021/0154433 A1* | 5/2021 | Casey | A61M 25/04 |
| 2021/0186537 A1 | 6/2021 | Buck et al. | |
| 2021/0186541 A1 | 6/2021 | Thress | |
| 2021/0205577 A1 | 7/2021 | Jalgaonkar et al. | |
| 2021/0236148 A1 | 8/2021 | Marchand et al. | |
| 2021/0251757 A1 | 8/2021 | Siegel et al. | |
| 2021/0275197 A1 | 9/2021 | Vale | |
| 2021/0290925 A1 | 9/2021 | Merritt et al. | |
| 2021/0315596 A1 | 10/2021 | Buck et al. | |
| 2021/0315598 A1 | 10/2021 | Buck et al. | |
| 2021/0316127 A1 | 10/2021 | Buck et al. | |
| 2021/0322166 A1 | 10/2021 | von Oepen et al. | |
| 2021/0330344 A1 | 10/2021 | Rosenbluth et al. | |
| 2021/0338984 A1 | 11/2021 | Booker et al. | |
| 2021/0361428 A1 | 11/2021 | Dixon | |
| 2021/0378648 A1 | 12/2021 | Thissen et al. | |
| 2021/0378692 A1 | 12/2021 | Xiang et al. | |
| 2021/0393276 A1 | 12/2021 | Whelan | |
| 2021/0393278 A1 | 12/2021 | O'Malley et al. | |
| 2021/0393280 A1 | 12/2021 | Villazon et al. | |
| 2021/0404464 A1 | 12/2021 | Patoskie | |
| 2022/0000500 A1 | 1/2022 | Arad Hadar et al. | |
| 2022/0000505 A1 | 1/2022 | Hauser | |
| 2022/0000506 A1 | 1/2022 | Hauser | |
| 2022/0000507 A1 | 1/2022 | Hauser | |
| 2022/0015784 A1 | 1/2022 | Erlick | |
| 2022/0015798 A1 | 1/2022 | Marchand et al. | |
| 2022/0021197 A1 | 1/2022 | Zhao et al. | |
| 2022/0022898 A1 | 1/2022 | Cox et al. | |
| 2022/0033888 A1 | 2/2022 | Schnall-Levin et al. | |
| 2022/0039815 A1 | 2/2022 | Thress et al. | |
| 2022/0047281 A1 | 2/2022 | Kamalova | |
| 2022/0125451 A1 | 4/2022 | Hauser | |
| 2022/0126060 A1 | 4/2022 | Shia et al. | |
| 2022/0142638 A1 | 5/2022 | Enright et al. | |
| 2022/0151647 A1 | 5/2022 | Dolendo et al. | |
| 2022/0152355 A1 | 5/2022 | Dolendo et al. | |
| 2022/0160381 A1 | 5/2022 | Hauser | |
| 2022/0160382 A1 | 5/2022 | Hauser | |
| 2022/0160383 A1 | 5/2022 | Hauser | |
| 2022/0211400 A1 | 7/2022 | Cox et al. | |
| 2022/0211992 A1 | 7/2022 | Merritt et al. | |
| 2022/0226555 A1 | 7/2022 | Sunenshine et al. | |
| 2022/0240959 A1 | 8/2022 | Quick | |
| 2022/0265964 A1 | 8/2022 | Asami et al. | |
| 2022/0288356 A1 | 9/2022 | Hiorth et al. | |
| 2022/0296797 A1 | 9/2022 | Chawla | |
| 2022/0330961 A1 | 10/2022 | Akpinar | |
| 2022/0331554 A1 | 10/2022 | Beasley et al. | |
| 2022/0346800 A1 | 11/2022 | Merritt et al. | |
| 2022/0346801 A1 | 11/2022 | Merritt et al. | |
| 2022/0346813 A1 | 11/2022 | Quick | |
| 2022/0346814 A1 | 11/2022 | Quick | |
| 2022/0347455 A1 | 11/2022 | Merritt et al. | |
| 2022/0362512 A1 | 11/2022 | Quick et al. | |
| 2022/0370761 A1 | 11/2022 | Chou et al. | |
| 2022/0378445 A1 | 12/2022 | Culbert et al. | |
| 2022/0378446 A1 | 12/2022 | Culbert et al. | |
| 2022/0378447 A1 | 12/2022 | Culbert et al. | |
| 2022/0378448 A1 | 12/2022 | Culbert et al. | |
| 2022/0378451 A1 | 12/2022 | Goyal et al. | |
| 2022/0378460 A1 | 12/2022 | Culbert et al. | |
| 2022/0387072 A1 | 12/2022 | Look et al. | |
| 2023/0015259 A1 | 1/2023 | Buck et al. | |
| 2023/0047682 A1 | 2/2023 | Deaton et al. | |
| 2023/0052964 A1 | 2/2023 | Singh et al. | |
| 2023/0059721 A1 | 2/2023 | Chou et al. | |
| 2023/0062809 A1 | 3/2023 | Merritt et al. | |
| 2023/0063701 A1 | 3/2023 | Horowitz et al. | |
| 2023/0070120 A1 | 3/2023 | Cox et al. | |
| 2023/0122587 A1 | 4/2023 | Chou et al. | |
| 2023/0145569 A1 | 5/2023 | McWeeney et al. | |
| 2023/0149034 A1 | 5/2023 | Aklog et al. | |
| 2023/0181200 A1 | 6/2023 | Deville et al. | |
| 2023/0200970 A1 | 6/2023 | Merritt et al. | |
| 2023/0210554 A1 | 7/2023 | Bruzzi et al. | |
| 2023/0218310 A1 | 7/2023 | Scheinblum et al. | |
| 2023/0218313 A1 | 7/2023 | Rosenbluth et al. | |
| 2023/0218383 A1 | 7/2023 | Merritt et al. | |
| 2023/0233311 A1 | 7/2023 | Merritt et al. | |
| 2023/0240705 A1 | 8/2023 | Rosenbluth et al. | |
| 2023/0240706 A1 | 8/2023 | Rosenbluth et al. | |
| 2023/0241302 A1 | 8/2023 | Merritt et al. | |
| 2023/0248380 A1 | 8/2023 | Long et al. | |
| 2023/0248498 A1 | 8/2023 | Buck et al. | |
| 2023/0248499 A1 | 8/2023 | Buck et al. | |
| 2023/0248500 A1 | 8/2023 | Buck et al. | |
| 2023/0248501 A1 | 8/2023 | Buck et al. | |
| 2023/0248502 A1 | 8/2023 | Buck et al. | |
| 2023/0248503 A1 | 8/2023 | Buck et al. | |
| 2023/0248504 A1 | 8/2023 | Buck et al. | |
| 2023/0270991 A1 | 8/2023 | Merritt et al. | |
| 2023/0310137 A1 | 10/2023 | Merritt et al. | |
| 2023/0310138 A1 | 10/2023 | Merritt et al. | |

(56)  References Cited

U.S. PATENT DOCUMENTS

| | | |
|---|---|---|
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |
| 2023/0355256 A1 | 11/2023 | Dinh |
| 2023/0355259 A1 | 11/2023 | Marchand et al. |
| 2023/0355371 A1 | 11/2023 | Buck et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0380850 A1 | 11/2023 | Vale et al. |
| 2023/0389932 A1 | 12/2023 | Ozenne et al. |
| 2023/0390045 A1 | 12/2023 | Merritt et al. |
| 2024/0016505 A1 | 1/2024 | Horowitz et al. |
| 2024/0016993 A1 | 1/2024 | Haslam et al. |
| 2024/0058113 A1 | 2/2024 | Strauss et al. |
| 2024/0074771 A1 | 3/2024 | Quick et al. |
| 2024/0081857 A1 | 3/2024 | Luong et al. |
| 2024/0082540 A1 | 3/2024 | Brodt et al. |
| 2024/0108366 A1 | 4/2024 | Horowitz et al. |
| 2024/0131235 A1 | 4/2024 | Horowitz et al. |
| 2024/0157041 A1 | 5/2024 | Zikry et al. |
| 2024/0173042 A1 | 5/2024 | Yang et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |
| 2024/0245501 A1 | 7/2024 | Strauss et al. |
| 2024/0245502 A1 | 7/2024 | Merritt et al. |
| 2024/0261492 A1 | 8/2024 | Yang et al. |
| 2024/0285387 A1 | 8/2024 | Merritt et al. |
| 2024/0299053 A1 | 9/2024 | Hauser |
| 2024/0307082 A1 | 9/2024 | Marchand et al. |
| 2024/0307166 A1 | 9/2024 | Merritt et al. |
| 2024/0341779 A1 | 10/2024 | Dinh |
| 2024/0341788 A1 | 10/2024 | Cox et al. |
| 2024/0407905 A1 | 12/2024 | Merrit et al. |
| 2024/0415626 A1 | 12/2024 | Merrit et al. |
| 2024/0415627 A1 | 12/2024 | Merrit et al. |
| 2025/0017618 A1 | 1/2025 | Truty et al. |
| 2025/0049456 A1 | 2/2025 | Cox et al. |
| 2025/0064464 A1 | 2/2025 | Barkley et al. |
| 2025/0090182 A1 | 3/2025 | Slaughter et al. |
| 2025/0161572 A1 | 5/2025 | Zikry et al. |
| 2025/0177625 A1 | 6/2025 | Merritt |
| 2025/0281192 A1 | 9/2025 | Quick et al. |

FOREIGN PATENT DOCUMENTS

| | | |
|---|---|---|
| AU | 2015218421 | 8/2017 |
| BR | PI0809253 | 9/2014 |
| CN | 1501825 | 6/2004 |
| CN | 102014772 | 4/2011 |
| CN | 102186427 | 9/2011 |
| CN | 102316809 | 1/2012 |
| CN | 103764049 | 4/2014 |
| CN | 103932756 | 7/2014 |
| CN | 104068910 | 10/2014 |
| CN | 105663841 | 6/2016 |
| CN | 106178227 | 12/2016 |
| CN | 106470728 | 3/2017 |
| CN | 106999271 | 8/2017 |
| CN | 108348319 | 7/2018 |
| CN | 110312481 | 10/2019 |
| CN | 110420046 | 11/2019 |
| CN | 110652645 | 1/2020 |
| CN | 111281482 | 6/2020 |
| CN | 112168286 | 1/2021 |
| CN | 112494102 | 3/2021 |
| CN | 112888384 | 6/2021 |
| CN | 214017710 | 8/2021 |
| CN | 113423348 | 9/2021 |
| CN | 113440217 | 9/2021 |
| CN | 215082793 | 12/2021 |
| CN | 215349271 | 12/2021 |
| CN | 114246639 | 3/2022 |
| CN | 215960137 | 3/2022 |
| CN | 216148140 | 4/2022 |
| CN | 114502086 | 5/2022 |
| DE | 1116001 | 10/1961 |
| DE | 102017004383 | 7/2018 |
| EP | 0432897 | 2/1996 |
| EP | 0914807 | 5/1999 |
| EP | 0956072 | 10/2001 |
| EP | 1254634 | 11/2002 |
| EP | 1663086 | 6/2006 |
| EP | 1267952 | 7/2008 |
| EP | 1937348 | 7/2008 |
| EP | 1991138 | 11/2008 |
| EP | 2073864 | 7/2009 |
| EP | 2203209 | 7/2010 |
| EP | 2209509 | 7/2010 |
| EP | 2394680 | 12/2011 |
| EP | 1867290 | 2/2013 |
| EP | 2624905 | 8/2013 |
| EP | 2540328 | 10/2013 |
| EP | 2726135 | 5/2014 |
| EP | 2908783 | 8/2015 |
| EP | 2939704 | 11/2015 |
| EP | 2942624 | 11/2015 |
| EP | 2967614 | 1/2016 |
| EP | 2977072 | 1/2016 |
| EP | 2367482 | 10/2016 |
| EP | 3102274 | 12/2016 |
| EP | 3122412 | 2/2017 |
| EP | 3202340 | 8/2017 |
| EP | 3302624 | 4/2018 |
| EP | 3305220 | 4/2018 |
| EP | 3305221 | 4/2018 |
| EP | 3311875 | 4/2018 |
| EP | 2231256 | 5/2018 |
| EP | 3344157 | 7/2018 |
| EP | 3417893 | 12/2018 |
| EP | 3419528 | 1/2019 |
| EP | 3422963 | 1/2019 |
| EP | 3439561 | 2/2019 |
| EP | 3449967 | 3/2019 |
| EP | 3544528 | 10/2019 |
| EP | 3583972 | 12/2019 |
| EP | 3589348 | 1/2020 |
| EP | 3603690 | 2/2020 |
| EP | 3612264 | 2/2020 |
| EP | 3620204 | 3/2020 |
| EP | 3013404 | 4/2020 |
| EP | 3705067 | 9/2020 |
| EP | 4039205 | 8/2022 |
| EP | 4301250 | 9/2022 |
| EP | 4072613 | 10/2022 |
| EP | 4076611 | 10/2022 |
| EP | 4079239 | 10/2022 |
| EP | 4079344 | 10/2022 |
| EP | 4137070 | 2/2023 |
| EP | 4144310 | 3/2023 |
| EP | 4252992 | 10/2023 |
| EP | 4419159 | 8/2024 |
| GB | 1588072 | 4/1981 |
| GB | 2498349 | 7/2013 |
| HK | 1162287 | 8/2012 |
| IN | 201837038624 | 10/2020 |
| IN | 202147016649 | 4/2021 |
| JP | H6190049 | 7/1994 |
| JP | H07323090 A | 12/1995 |
| JP | 2001522631 | 5/1999 |
| JP | 2004097807 | 4/2004 |
| JP | 2005511989 | 4/2005 |
| JP | 2005-095242 | 6/2005 |
| JP | 2005230132 | 9/2005 |
| JP | 2005323702 | 11/2005 |
| JP | 2006094876 | 4/2006 |
| JP | 2007-222658 | 9/2007 |
| JP | 2011526820 | 1/2010 |
| JP | 2011517424 | 6/2011 |
| JP | 2012213478 | 11/2012 |
| JP | 05694718 | 4/2015 |

(56) References Cited

FOREIGN PATENT DOCUMENTS

| | | |
|---|---|---|
| JP | 2015208685 | 11/2015 |
| JP | 2016513505 | 5/2016 |
| JP | 2016104212 | 6/2016 |
| JP | 2017533051 | 11/2017 |
| JP | 6325543 | 5/2018 |
| JP | 2018525088 | 9/2018 |
| JP | 2022104828 | 7/2022 |
| JP | 2003033359 | 2/2023 |
| JP | 7253376 | 3/2023 |
| JP | 7324264 | 8/2023 |
| JP | 7491974 | 5/2024 |
| KR | 2018045822 | 5/2018 |
| KR | 2020133754 | 11/2020 |
| TW | 7778088 | 9/2022 |
| WO | WO1997017889 | 5/1997 |
| WO | WO1998024501 | 6/1998 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO9951140 | 10/1999 |
| WO | WO0032118 | 6/2000 |
| WO | WO2000053120 | 9/2000 |
| WO | WO0202162 | 1/2002 |
| WO | WO2002053221 | 7/2002 |
| WO | WO2002055146 | 7/2002 |
| WO | WO03015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2008039684 | 4/2008 |
| WO | WO2009082513 | 7/2009 |
| WO | WO2009086482 | 7/2009 |
| WO | WO2009105710 | 8/2009 |
| WO | WO2009126747 | 10/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010095712 | 8/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012114633 | 8/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2014139845 | 9/2014 |
| WO | WO2014207797 | 12/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018100445 | 6/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO-2019173475 A1 * | 9/2019 ....... A61B 17/00234 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2020162724 | 8/2020 |
| WO | WO2021020767 | 2/2021 |
| WO | WO2021067134 | 4/2021 |
| WO | WO2021076954 | 4/2021 |
| WO | WO2021127202 | 6/2021 |
| WO | WO2021162678 | 8/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2022214020 | 10/2022 |
| WO | WO2022221643 | 10/2022 |
| WO | WO2022223772 | 10/2022 |
| WO | WO2022261448 | 12/2022 |
| WO | WO2023018819 | 2/2023 |
| WO | WO2023069874 | 4/2023 |
| WO | WO2003048616 | 6/2023 |
| WO | WO2023115032 | 6/2023 |
| WO | WO2023137341 | 7/2023 |
| WO | WO2023143700 | 8/2023 |
| WO | WO2023147353 | 8/2023 |
| WO | WO2023154612 | 8/2023 |
| WO | WO2023178212 | 9/2023 |
| WO | WO2023192925 | 10/2023 |
| WO | WO2023215779 | 11/2023 |
| WO | WO2023239706 | 12/2023 |
| WO | WO2024006482 | 1/2024 |
| WO | WO2024044710 | 2/2024 |
| WO | WO2024054988 | 3/2024 |
| WO | WO2024059695 | 3/2024 |
| WO | WO2024103036 | 5/2024 |
| WO | WO2024151629 | 7/2024 |
| WO | WO2025014517 | 1/2025 |
| WO | WO2025059542 | 3/2025 |
| WO | WO2025106851 | 5/2025 |
| WO | WO2025111572 | 5/2025 |
| WO | WO2025117864 | 6/2025 |
| WO | WO2025188578 | 9/2025 |

OTHER PUBLICATIONS

US 12,115,056 B2, 10/2024, Merritt et al. (withdrawn)

Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, mailed Jan. 17, 2014, 7 pages.

International Search Report and Written Opinion for International App. No. PCT/US2014/046567, mailed Nov. 3, 2014, 13 pages.

International Search Report and Written Opinion for International App. No. PCT/US2014/061645, mailed Jan. 23, 2015, 15 pages.

International Search Report for International App. No. PCT/US13/71101, mailed Mar. 31, 2014, 4 pages.

(56) References Cited

OTHER PUBLICATIONS

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc, Ther. 8(6), 863-873 (2010).

Liu, S. et al., "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.

Spiotta, A et al., "Evolution of thrombectorny approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

Truong et al., "Mechanical Thrombectomy of Iliocaval Thrombosis Using a Protective Expandable Sheath," Cardiovasc Intervent Radiol27-254-258, 2004, 5 pgs.

Turk et al., "Adapt Fast study: a direct aspiration first pass technique for acute stroke thrombectomy." J Neurointervent Surg, vol. 6, 2014, 6 pages.

Uflacker, R., "Interventional Therapy for Pulmonary Embolism", Journal of Vascular and Interventional Radiology, Feb. 2001: 12:147-164.

Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.

International Search Report and Written Opinion for International App. No. PCT/US2015/034987 filed Jun. 9, 2015, Applicant: Inceptus Medical, LLC, Date of Mailing: Sep. 17, 2015, 12 pages.

English translation of Japanese Office Action received for JP Application No. 2016-564210, Applicant: Inceptus Medical, LLC, Date of Mailing: Sep. 4, 2017, 4 pages.

International Search Report and Written Opinion for International App. No. PCT/US2016/067628 filed Dec. 19, 2016, Applicant: Inari Medical, Inc., Date of Mailing: Apr. 10, 2017, 11 pages.

Goldhaber, S. et al. "Percutaneous Mechanical Thrombectomy for Acute Pulmonary Embolism—A Double-Edged Sword," American College of CHEST Physicians, Aug. 2007, 132:2, 363-372.

Goldhaber, S., "Advanced treatment strategies for acute pulmonary embolism, including thrombolysis and embolectomy," Journal of Thrombosis and Haemostasis, 2009: 7 (Suppl. 1): 322-327.

International Search Report and Written Opinion for International App. No. PCT/US2017/029696, Date of Filing: Apr. 26, 2017, Applicant: Inari Medical, Inc., Date of Mailing: Sep. 15, 2017, 19 pages.

International Search Report and Written Opinion for International App. No. PCT/US2016/058536, Date of Filing: Oct. 24, 2016, Applicant: Inari Medical, Inc., Date of Mailing: Mar. 13, 2017, 14 pages.

International Search Report and Written Opinion for International App. No. PCT/US2018/048786, Date of Filing: Aug. 30, 2018, Applicant: Inari Medical, Inc., Date of Mailing: Dec. 13, 2018, 12 pages.

International Search Report and Written Opinion for International App. No. PCT/US2018/055780, Date of Filing: Oct. 13, 2018, Applicant: Inceptus Medical LLC., Date of Mailing: Jan. 22, 2019, 8 pages.

International Search Report and Written Opinion for International App. No. PCT/US2019/045794, Date of Filing: Aug. 8, 2019, Applicant: Inari Medical, Inc., Date of Mailing: Nov. 1, 2019, 17 pages.

International Search Report and Written Opinion for International App. No. PCT/US2020/056067, Date of Filing: Oct. 16, 2020; Applicant: Inari Medical, Inc., Date of Mailing: Jan. 22, 2021, 8 pages.

International Search Report and Written Opinion for International App. No. PCT/US2020/055645, Date of Filing: Dec. 17, 2020; Applicant: Inari Medical, Inc., Date of Mailing: Apr. 14, 2021, 12 pages.

Vorwerk, D. MD, et al., "Use of a Temporary Caval Filter to Assist Percutaneous Illocaval Thrombectomy: Experimental Results." SCVIR, 1995, 4 pages.

Wikipedia; Embolectomy; retrieved from the internet: https://en.wikipedia.org/wiki/Embolectomy; 4 pgs.; retrieved/printed: Mar. 24, 2016.

O'Sullivan; Thrombolysis versus thrombectomy in acute deep vein thrombosis; Interventional Cardiology; 3(5); pp. 589-596; Oct. 2011.

Capture Vascular Systems; (company website); retrieved from the internet: http://www.capturevascular.com; 3 pgs.; retrieved/printed: Mar. 24, 2016.

Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.

Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.

(56)          References Cited

OTHER PUBLICATIONS

Penumbra, Inc.; Indigo® System (product information); retrieved from the internet: http://www.penumbrainc.com/peripherallpercutane-ous-thromboembolectomy/indigo-system; 7 pgs.; retrieved/printed: Mar. 24, 2016.

Youtube; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.

Covidien; Solitaire(TM) AS Neurovascular Remodeling Device (product information); retrieved from the internet: http://www.ev3.net/neuro/intl/remodeling-devices/solitaire-ab. htm; © 2015; 2 pgs.; retrieved/printed: Mar. 24, 2016.

International Search Report and Written Opinion for International App. No. PCT/US21/35965, Date of Filing: Jun. 4, 2021, Applicant: Inari Medical, Inc., Date of Mailing: Sep. 28, 2021, 12 pages.

International Search Report and Written Opinion for International App. No. PCT/US21/45072 Date of Filing: Aug. 6, 2021, Applicant: Inari Medical, Inc., Date of Mailing: Jan. 20, 2022, 10 pages.

International Search Report and Written Opinion for International App. No. PCT/US21/58793; Date of Filing: Nov. 10, 2021, Applicant: Inari Medical, Inc., Date of Mailing: Mar. 16, 2022, 13 pages.

International Search Report and Written Opinion for International App. No. PCT/US21/59718; Date of Filing: Nov. 17, 2021, Applicant: Inari Medical, Inc., Date of Mailing: Mar. 22, 2022, 13 pages.

International Search Report and Written Opinion for International App. No. PCT/US21/59735; Date of Filing: Nov. 17, 2021, Applicant: Inari Medical, Inc., Date of Mailing: Mar. 22, 2022, 11 pages.

International Search Report and Written Opinion for International App. No. PCT/US23/60502; Date of Filing: Jan. 11, 2023, Applicant: Inari Medical, Inc., Date of Mailing: May 25, 2023, 9 pages.

International Search Report and Written Opinion for International App. No. PCT/US23/61256; Date of Filing: Jan. 25, 2023, Applicant: Inari Medical, Inc., Date of Mailing: Jun. 7, 2023, 8 pages.

International Search Report and Written Opinion for International App. No. PCT/US23/60927; Date of Filing: Jan. 19, 2023, Applicant: Inari Medical, Inc., Date of Mailing: Jul. 20, 2023, 12 pages.

Extended European Search Report issued for EP Application No. 20877370.5, Date of Mailing: Oct. 17, 2023, 11 pages.

International Search Report and Written Opinion for International App. No. PCT/US23/65128; Date of Filing: Mar. 30, 2023, Applicant: Inari Medical, Inc., Date of Mailing: Nov. 14, 2023, 14 pages.

International Search Report and Written Opinion for International App. No. PCT/US23/66538; Date of Filing: May 3, 2023, Applicant: Inari Medical, Inc., Date of Mailing: Jan. 4, 2024, 14 pages.

English translation of Japanese Office Action received for JP Application No. 2022-574456, Applicant: Inari Medical, Inc, Date of Mailing: Jan. 23, 2024, 12 pages.

Chinese First Office Action received for CN Application No. 201980067623.1, Applicant: Inari Medical, Inc., Date of Mailing: Jan. 31, 2024, 10 pages.

International Search Report and Written Opinion for International App. No. PCT/US23/73765; Date of Filing: Sep. 8, 2023, Applicant: Inari Medical, Inc., Date of Mailing: Feb. 28, 2024, 7 pages.

International Search Report and Written Opinion for International App. No. PCT/US23/69892; Date of Filing: Jul. 10, 2023, Applicant: Inari Medical, Inc., Date of Mailing: Feb. 29, 2024, 12 pages.

English translation of Japanese Office Action mailed Jan. 19, 2024 for Japanese Application No. 2022-160947, 8 pages.

English machine translation of Japanese Office Action mailed Oct. 10, 2024 for Japanese Application No. 2022-522892, 11 pages.

International Search Report and Written Opinion for International App. No. PCT/US2024/043504; Applicant: Inari Medical, Inc., Date of Mailing: Nov. 12, 2024, 12 pages.

International Search Report and Written Opinion for International App. No. PCT/US2024/037570; Applicant: Inari Medical, Inc., Date of Mailing: Nov. 20, 2024, 12 pages.

International Search Report and Written Opinion for International App. No. PCT/US2024/046723; Applicant: Inari Medical, Inc., Date of Mailing: Nov. 27, 2024, 11 pages.

International Search Report and Written Opinion for International App. No. PCT/US2024/010875; Applicant: Inari Medical, Inc., Date of Mailing: Apr. 26, 2024, 15 pages.

International Search Report and Written Opinion for International App. No. PCT/US2023/079428; Applicant: Inari Medical, Inc., Date of Mailing: May 29, 2024, 18 pages.

Extended European Search Report for European Application No. 21818772.2, Applicant: Inari Medical, Inc., Date of Mailing: May 10, 9 pages.

Chinese Office Action received for Application No. 202111061740. 2, Applicant: Inari Medical, Inc, Date of Mailing: May 23, 2024, 15 pages.

English translation of Japanese Office Action mailed Jun. 25, 2024 for Japanese Application No. 2022-574456, 5 pages.

Japanese Office Action mailed Jul. 8, 2024 for Japanese Application No. 2022-522892, 14 pages.

Chinese first Office Action mailed May 10, 2024 for Chinese Application No. 202080087833.X, 11 pages.

Partial Supplementary European Search Report received for European Application No. 21852966.7; Applicant: Inari Medical, Inc., Date of Mailing: Jul. 23, 2024, 12 pages.

Japanese Office Action mailed Aug. 2, 2024 for Japanese Application No. 2023-213724, 3 pages.

English Translation of Japanese Office Action mailed Jul. 23, 2024 for Japanese Application No. 2022- 535535, 11 pages.

Extended European Search Report received for European Application No. 21895504.5; Applicant: Inari Medical, Inc., Date of Mailing: Aug. 16, 2024, 10 pages.

English translation of Japanese Office Action mailed Sep. 17, 2024 for Japanese Application No. 2023-203650, 6 pages.

English translation of Japanese Office Action for Japanese Application No. 2024-064603 mailed May 16, 2025, 4 pages.

International Search Report and Written Opinion for International App. No. PCT/US2025/038708; Applicant: Inari Medical, Inc., Date of Mailing: Sep. 18, 2025, 11 pages.

English translation of Chinese Office Action mailed Jan. 22, 2025 for Chinese Application No. 202210842779.6, 17 pages.

Extended European Search Report received for European Application No. 24209030.6; Applicant: Inari Medical, Inc., Date of Mailing: Feb. 3, 2025, 7 pages.

International Search Report and Written Opinion for International App. No. PCT/US2024/056178; Applicant: Inari Medical, Inc., Date of Mailing: Mar. 24, 2025, 13 pages.

International Search Report and Written Opinion for International App. No. PCT/US2024/057919; Applicant: Inari Medical, Inc., Date of Mailing: Mar. 28, 2025, 13 pages.

English translation of Chinese Second Office Action mailed Apr. 24, 2025 for Chinese Application No. 202080097026.6, 10 pages.

International Search Report for International Application No. PCT/US2023/026648, mailed on Dec. 19, 2023, 6 pages.

Written Opinion of the International Searching Authority for International Application No. PCT/US2023/026648, dated Dec. 19, 2023, 31 pages.

Bayer HealthCare, 'Our Next Generation Aspiration Catheter.' Fetch 2 Catheter Specifications, Feb. 2013, 2 pages.

Medtronic, Solitaire X, Revascularization Device. http://www.ev3.net/neuro/intl/remodeling-devices/solitaire-ab.htm. 6 pages, (2019).

International Search Report and Written Opinion for International App. No. PCT/US2023/074169; Applicant: Inari Medical, Inc., Date of Mailing: May 1, 2024, 12 pages.

English translation of Japanese Office Action for Japanese Application No. 2023-507628, mailed Apr. 23, 2025, 8 pages.

* cited by examiner

670

Internal jugular vein

100

102

Superior vena cava

Heart

Inferior vena cava

672

120

564

Common iliac veins

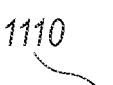

*1110*

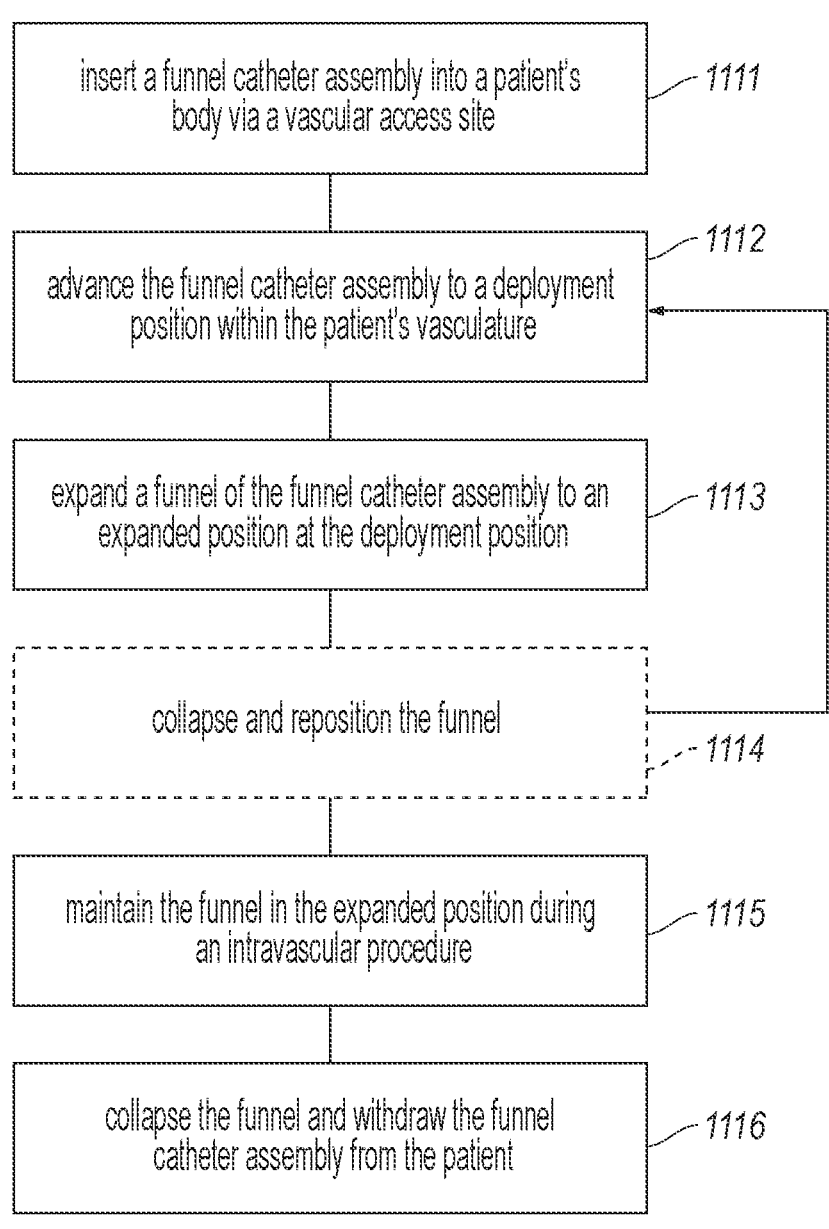

insert a funnel catheter assembly into a patient's body via a vascular access site — *1111* advance the funnel catheter assembly to a deployment position within the patient's vasculature — *1112* expand a funnel of the funnel catheter assembly to an expanded position at the deployment position — *1113* collapse and reposition the funnel — *1114* maintain the funnel in the expanded position during an intravascular procedure — *1115* collapse the funnel and withdraw the funnel catheter assembly from the patient — *1116*

*Fig. 11*

RECAPTURABLE FUNNEL CATHETERS, AND ASSOCIATED SYSTEMS AND METHODS

CROSS-REFERENCE TO RELATED APPLICATION

This application claims the benefit of U.S. Provisional Patent Application No. 63/035,605, filed Jun. 5, 2020, and titled "RECAPTURABLE FUNNEL CATHETERS, AND ASSOCIATED SYSTEMS AND METHODS," which is incorporated herein by reference in its entirety.

TECHNICAL FIELD

The present technology generally relates to systems, methods, and devices for embolic protection during procedures for extracting thrombi from blood vessels of human patients.

BACKGROUND

Thrombosis is the local coagulation or clotting of the blood in a part of the circulatory system, and a thrombus is a blood clot formed in situ within the vascular system. A venous thrombus is a blood clot that forms within a vein. A common type of venous thrombosis is a deep vein thrombosis (DVT), which is the formation of a blood clot within a deep vein (e.g., predominantly in the legs). Nonspecific signs of a thrombosis may include pain, swelling, redness, warmness, and engorged superficial veins.

If the thrombus breaks off (embolizes) and flows towards the lungs, it can become a life-threatening pulmonary embolism (PE) (e.g., a blood clot in the lungs). In addition to the loss of life that can arise from PE, DVT can cause significant health issues such as post thrombotic syndrome, which can cause chronic swelling, pressure, pain, and ulcers due to valve and vessel damage. Further, DVT can result in significant health-care costs either directly or indirectly through the treatment of related complications and inability of patients to work.

Three processes are believed to result in venous thrombosis. First is a decreased blood flow rate (venous stasis), second is an increased tendency to clot (hypercoagulability), and the third is changes to the blood vessel wall. DVT formation typically begins inside the valves of the calf veins where the blood is relatively oxygen deprived, which activates certain biochemical pathways. Several medical conditions increase the risk for DVT, including diabetes, cancer, trauma, and antiphospholipid syndrome. Other risk factors include older age, surgery, immobilization (as with bed rest, orthopedic casts, and sitting on long flights), combined oral contraceptives, pregnancy, the postnatal period, and genetic factors. The rate of DVT increases dramatically from childhood to old age and, in adulthood, about 1 in 1,000 adults develop DVT annually.

Although current devices and methods of prevention and/or treatment of DVT exist, there are a number of shortcomings that have yet to be resolved, such as high incidence of DVT re-occurrence, use of devices not designed to remove large clot volumes, and/or complicated treatments involving multiple treatment devices and/or pharmaceuticals. Accordingly, new devices, systems, and methods of treating thrombus, and particularly DVT are desired.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 11 is a flow diagram of a process or method for operating the funnel catheter assembly during an intravascular procedure in accordance with embodiments of the present technology.

DETAILED DESCRIPTION

Figure 1:
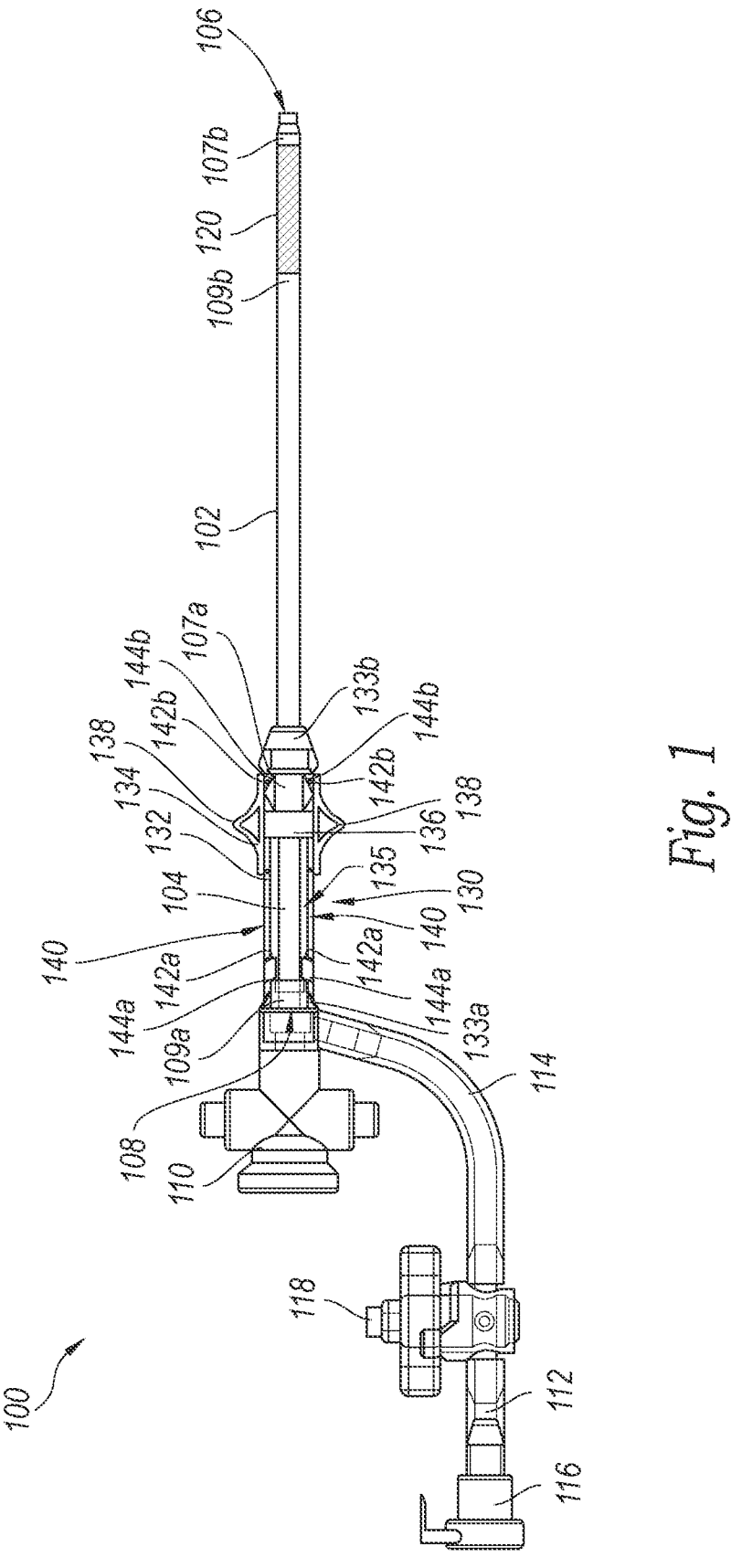
FIG. 1 is a partially transparent and partially cross-sectional side view of a funnel catheter assembly in accordance with embodiments of the present technology.

The present technology is generally directed to methods and systems for removing clot material (e.g., a thrombus) from a blood vessel of a human patient. More particularly, the present technology is directed to funnel catheter assemblies configured to provide embolic protection during a clot removal or other intravascular procedure. In some embodiments, a funnel catheter assembly includes an outer shaft and an inner shaft extending through and coaxial with the outer shaft. An expandable funnel, such as a self-expanding funnel, can be coupled to a distal portion of the inner shaft. The funnel catheter assembly further includes a control assembly operably coupled to the proximal portion of the outer shaft. The funnel catheter assembly can be actuated by an operator (e.g., a physician) to move the outer shaft between a first position and a second position. In the first position, the outer shaft is positioned at least partially over the funnel to constrain the funnel in a compressed state. In the second position, the outer shaft is retracted proximally relative to the funnel such that the funnel can expand to an expanded state. Accordingly, the funnel catheter assembly enables the funnel to be unsheathed and sheathed during an intravascular procedure via the movement of the outer shaft between the first and second positions.

In one aspect of the present technology, the control assembly is operable to compress the funnel after it has been expanded within a blood vessel of a patient. This can permit the funnel catheter assembly to be repositioned within the blood vessel without fully withdrawing the funnel catheter assembly from the patient. Similarly, the funnel catheter assembly can be fully withdrawn from the patient (e.g., at the conclusion of a thrombectomy procedure) in the first position with the funnel compressed inside the outer shaft. Thus, the funnel catheter assembly is configured to inhibit or even prevent the funnel from contacting the wall of the blood vessel during movement of the funnel catheter assembly within the blood vessel. This can help inhibit injury/damage to the patient that could otherwise be caused by the moving the funnel through a blood vessel or an associated organ in the expanded state.

Although many of the embodiments are described below with respect to devices, systems, and methods for treating vascular thrombi (e.g., deep vein thrombosis (DVT)), other applications and other embodiments in addition to those described herein are within the scope of the technology (e.g., intravascular procedures other than the treatment of emboli, intravascular procedures for treating cerebral embolism, intravascular procedures for treating pulmonary embolism, etc.). In general, for example, the devices, systems, and methods of the present technology can be used to extract any formation of material in a vessel (e.g., a venous or arterial vessel), such as cancerous growths, vegetation, etc. Additionally, several other embodiments of the technology can have different configurations, states, components, or procedures than those described herein. Moreover, it will be appreciated that specific elements, substructures, advantages, uses, and/or other features of the embodiments described with reference to FIGS. 1-11 can be suitably interchanged, substituted or otherwise configured with one another in accordance with additional embodiments of the present technology. Furthermore, suitable elements of the embodiments described with reference to FIGS. 1-11 can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1-11.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," etc. are not meant to limit the referenced component to use in a specific orientation. It will be appreciated that such designations refer to the orientation of the referenced component as illustrated in the Figures; the systems of the present technology can be used in any orientation suitable to the user.

The headings provided herein are for convenience only and should not be construed as limiting the subject matter disclosed.

I. SELECTED EMBODIMENTS OF FUNNEL CATHETER ASSEMBLIES

FIG. 1 is a partially transparent and partially cross-sectional side view of a funnel catheter assembly 100 in accordance with embodiments of the present technology. In the illustrated embodiment, the funnel catheter assembly 100 includes an elongate outer shaft 102 and an elongate inner shaft 104 coaxial with the outer shaft 102. The outer and inner shafts 102, 104 ("shafts 102, 104") can also be referred to as sheaths, catheters, hollow members, and so on. The outer shaft 102 defines a lumen 106 and includes a proximal portion 107a and a distal portion 107b. The inner shaft 104 extends through the lumen 106 of the outer shaft 102 and similarly defines a lumen 108 and includes a proximal portion 109a and a distal portion 109b. The proximal portions 107a and 109a can each terminate at a proximal end/terminus, and the distal portions 107b and 109b can each terminate at a distal end/terminus. The shafts 102, 104 can be elastic and/or flexible and can have any suitable length and diameter.

In the illustrated embodiment, the funnel catheter assembly 100 further includes a sealable hub 110 coupled to the proximal portion 109a of the inner shaft 104. In some embodiments, as described in greater detail below with reference to FIGS. 9A-9C, the sealable hub 110 can be rotatable coupled to the inner shaft 104 such that the sealable hub 110 can rotate independently of the inner shaft 104. The sealable hub 110 is configured to allow access to the lumen 108 of the inner shaft 104 and can be self-sealing and/or can comprise a self-sealing seal. For example, in the illustrated embodiment the sealable hub 110 is a hemostasis valve that is configured to maintain hemostasis (e.g., during a thrombus extraction procedure) by inhibiting or even preventing fluid flow in the proximal direction through the sealable hub 110 as, for example, various components (e.g., dilator assemblies, thrombus extraction devices, etc.) are inserted through the sealable hub 110 to be delivered through the inner shaft 104 to a treatment site in a blood vessel. More specifically, the sealable hub 110 can be a valve of the type disclosed in U.S. patent application Ser. No. 16/117,519, filed Aug. 30, 2018, and titled "HEMOSTASIS VALVES AND METHODS OF USE," which is incorporated herein by reference in its entirety. The sealable hub 110 can include one or more buttons or actuators that enable an operator to selectively seal/unseal the sealable hub 110.

The funnel catheter assembly 100 can further include an aspiration port 112 connected to the sealable hub 110 (e.g., to a side port of the sealable hub 110) and/or the inner shaft 104 (e.g., to the proximal portion 109a of the inner shaft 104) via, for example, a connecting tube 114. The aspiration port 112 can be connected to a syringe connector 116 that can be selectively coupled to a syringe or other aspiration device, or the aspiration port 112 can be connected to other suitable elements. In some embodiments, the funnel catheter assembly 100 includes a fluid control device 118 configured to selectively fluidly connect the aspiration port 112 to the lumen 108 of the inner shaft 104. In the illustrated embodiment, the fluid control device 118 is a stopcock operably coupled to the connecting tube 114 between the lumen 108 of the inner shaft 104 and the aspiration port 112. In other embodiments, the fluid control device 118 can be a clamp or another suitable valve. In some embodiments, a vacuum source (not shown; e.g., a syringe) can be coupled to the syringe connector 116 and used to aspirate the lumen 108 of the inner shaft 104. In some embodiments, as described in greater detail below with reference to FIGS. 9A-9C, the aspiration port 112 and the connecting tube 114 can be rotatable relative to the sealable hub 110 and/or the inner shaft 104.

In the illustrated embodiment, a funnel 120 is coupled to the distal portion 109b of the inner shaft 104. As described in greater detail below, in operation of the funnel catheter assembly 100 during an intravascular procedure, the funnel 120 is configured to expand (e.g., radially expand) into apposition with a blood vessel and/or other bodily lumen (e.g., of an organ) and act as a proximal or distal thrombus/embolic protection device that inhibits any thrombus from moving past the funnel 120 and embolizing in an unwanted location (e.g., the right heart, the pulmonary arteries, another arterial space, etc.). The funnel 120 can be fused to the distal portion 109b of the inner shaft 104, and/or attached to the inner shaft 104 via welding, adhesives, fasteners, etc. In FIG. 1, the funnel catheter assembly 100 is in a first position/state/configuration in which the distal portion 107*b* of the outer shaft 102 extends beyond the distal portion 109*b* of the inner shaft 104 such that the funnel 120 is at least partially (e.g., entirely) positioned within the lumen 106 of the outer shaft 102. The funnel 120 can be configured to expand (e.g., self-expand) and, accordingly, the funnel 120 can be in a first, constrained position/state/configuration when the funnel catheter assembly 100 is in the first position. In some embodiments, the funnel 120 can be formed from at least one of a castellated nitinol braid, a nitinol braided stent, a laser cut nitinol, a laser cut polymer tube, an injection molded polymeric structure, or an inflatable balloon. In some embodiments, the funnel 120 can comprise a mesh having a pore size sufficiently small to prevent the passage of thrombus through the pores of the mesh. In some embodiments, the funnel 120 can be permeable to blood. In some embodiments, the funnel 120 can include a covering over at least a portion thereof that is permeable or non-permeable to blood.

In the illustrated embodiment, the proximal portion 107*a* of the outer shaft 102 is operably coupled to a control assembly 130. The control assembly 130 is operable to move the outer shaft 102 distally and proximally relative to the inner shaft 104 to constrain and release the funnel 120 from within the lumen 106 of the outer shaft 102. More specifically, in the illustrated embodiment the control assembly 130 includes (i) a housing 132 having a proximal portion 133*a* and a distal portion 133*b*, and (ii) an actuation member 134 operably/movably coupled to the housing 132. The housing 132 defines a lumen 135 extending between the proximal and distal portions 133*a, b* thereof. The proximal portion 133*a* of the housing 132 can be coupled to the sealable hub 110. In some embodiments, the proximal portion 133*a* of the housing 132 is integrally formed with the sealable hub 110.

In the illustrated embodiment, the actuation member 134 includes a body portion 136 positioned within the lumen 135 of the housing 132 and coupled to the proximal portion 107*a* of the outer shaft 102 via, for example, adhesive, fasteners, welding, etc. The actuation member 134 further includes one or more grip members 138 extending from the body portion 136 to outside of the lumen 135. More specifically, the grip members 138 can extend through corresponding slots 140 formed in/along the housing 132. The housing 132 can define a proximal terminus 142*a* and a distal terminus 142*b* for each of the slots 140. In some embodiments, the control assembly 130 can include one, or more than the illustrated two of the grip members 138 and corresponding slots 140.

Figures 2A, 2B:
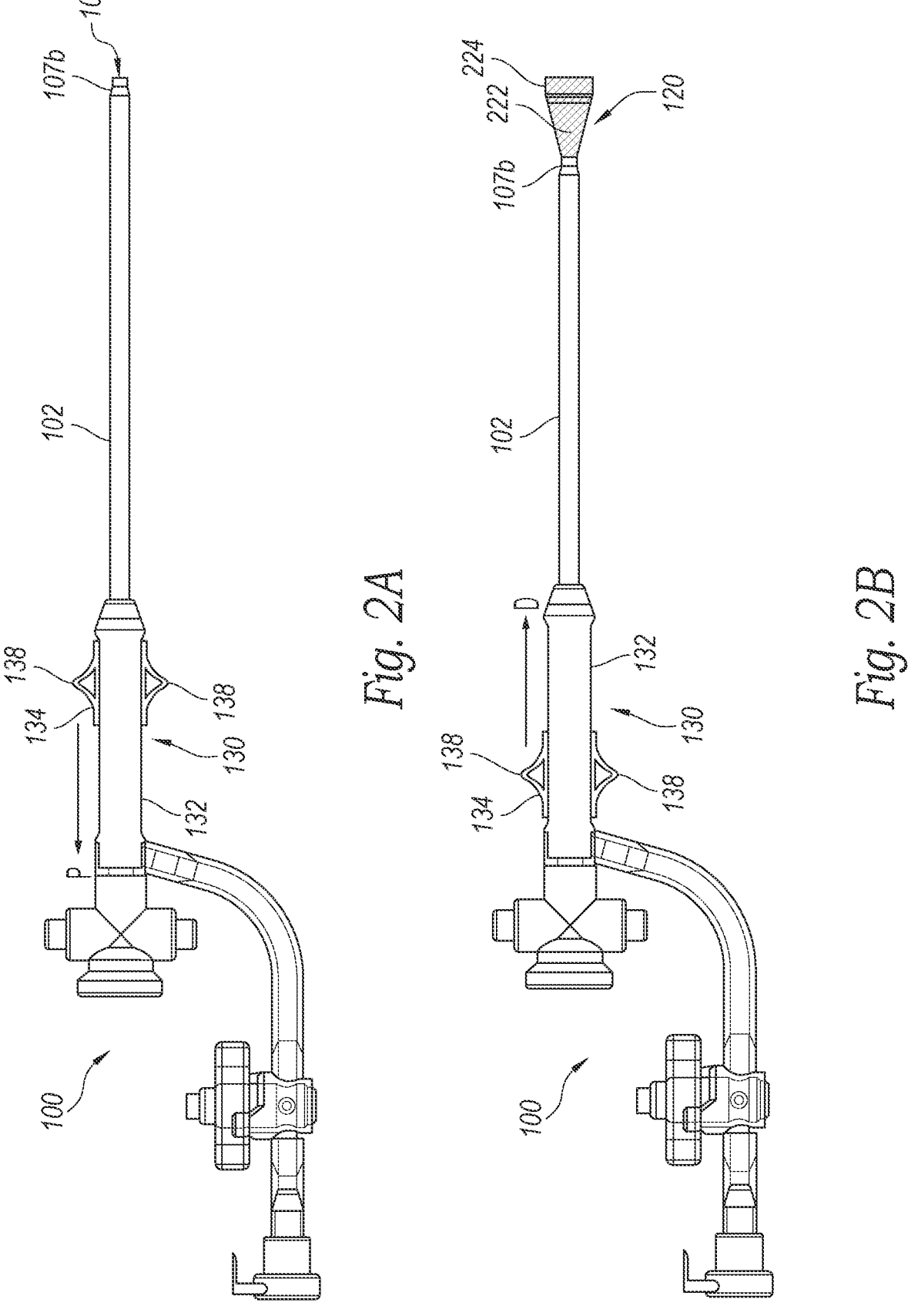
FIGS. 2A and 2B are side views of the funnel catheter assembly in a first position and a second position, respectively, in accordance with embodiments of the present technology.

In operation, an operator (e.g., a physician) can slide the actuation member 134 along the housing 132 to distally advance and proximally retract the outer shaft 102 relative to the inner shaft 104 to constrain and release the funnel 120, respectively. More specifically, FIGS. 2A and 2B are side views of the funnel catheter assembly 100 in the first position and in a second position, respectively, in accordance with embodiments of the present technology. Referring to FIGS. 1-2B together, to move the funnel catheter assembly 100 from the first position (FIGS. 1 and 2A) to the second position (FIG. 2B), the operator can grip the grip members 138 of the actuation member 134 and slide the grip members 138 proximally (e.g., in the direction of arrow P in FIG. 2A) relative to the housing 132 to drive the body portion 136 through the lumen 135 to thereby drive the outer shaft 102 proximally relative to the inner shaft 104. The funnel 120 is released/unsheathed from within the lumen 106 of the outer shaft 102 as the distal portion 107*b* of the outer shaft 102 moves proximally past the funnel 120, thereby allowing the funnel 120 to expand. In some embodiments, the actuation member 134 can abut the proximal termini 142*a* of the slots 140 in the second position such that the housing 132 inhibits further proximal movement of the outer shaft 102.

In some embodiments, the distal terminus of the outer shaft 102 is positioned at or proximal of the distal terminus of the inner shaft 104 in the second position such that the funnel 120 is fully released from (e.g., positioned fully outside of) the lumen 106 of the outer shaft 102. In other embodiments, the distal terminus of the outer shaft 102 can be positioned distal of the distal terminus of the inner shaft 104 in the second position such that the funnel 120 is only partially released from the lumen 106 of the outer shaft 102. Moreover, as shown in FIG. 2B, the funnel 120 can have a conically shaped portion 222 (e.g., a truncated-conically shaped portion) and a cylindrical portion 224 once expanded. In other embodiments, the funnel 120 can have other suitable shapes. For example, in some embodiments the funnel 120 can be inverted relative to the embodiment shown in FIG. 2B. That is, the cylindrical portion 224 of the funnel 120 can be coupled to the distal portion 109*b* of the inner shaft 104 while the conically shaped portion 222 extends distally from the cylindrical portion 224.

To move the funnel catheter assembly 100 from the second position (FIG. 2B) to the first position (FIGS. 1 and 2A), the operator can grip the grip members 138 of the actuation member 134 and slide the grip members 138 distally (e.g., in the direction of arrow D in FIG. 2B) relative to the housing 132 to drive the body portion 136 through the lumen 135 to thereby drive the outer shaft 102 distally relative to the inner shaft 104. The funnel 120 is captured/sheathed in the lumen 106 of the outer shaft 102 as the distal portion 107*b* of the outer shaft 102 moves distally over the funnel 120, thereby collapsing/compressing the funnel 120 within the lumen 106. In some embodiments, the actuation member 134 can abut the distal termini 142*b* of the slots 140 in the first position such that the housing 132 inhibits further distal movement of the outer shaft 102.

In some embodiments the actuation member 134 is configured to be releasably secured/locked to the housing 132 in the first and second positions to inhibit or even prevent unintended movement of the actuation member 134. For example, referring again to FIG. 1, the housing 132 of the control assembly 130 can include (i) proximal engagement members 144*a* (e.g., tabs, protrusions, etc.) configured to engage the actuation member 134 in the first position and (ii) distal engagement members 144*b* configured to engage the actuation member 134 in the second position. More specifically, in some embodiments the proximal and distal engagement members 144*a, b* can mate with corresponding slots/grooves in the actuation member 134 (e.g., formed in/on the grip members 138) to releasably secure the actuation member 134 in the first or second positions via a snap fit arrangement.

Figure 3:
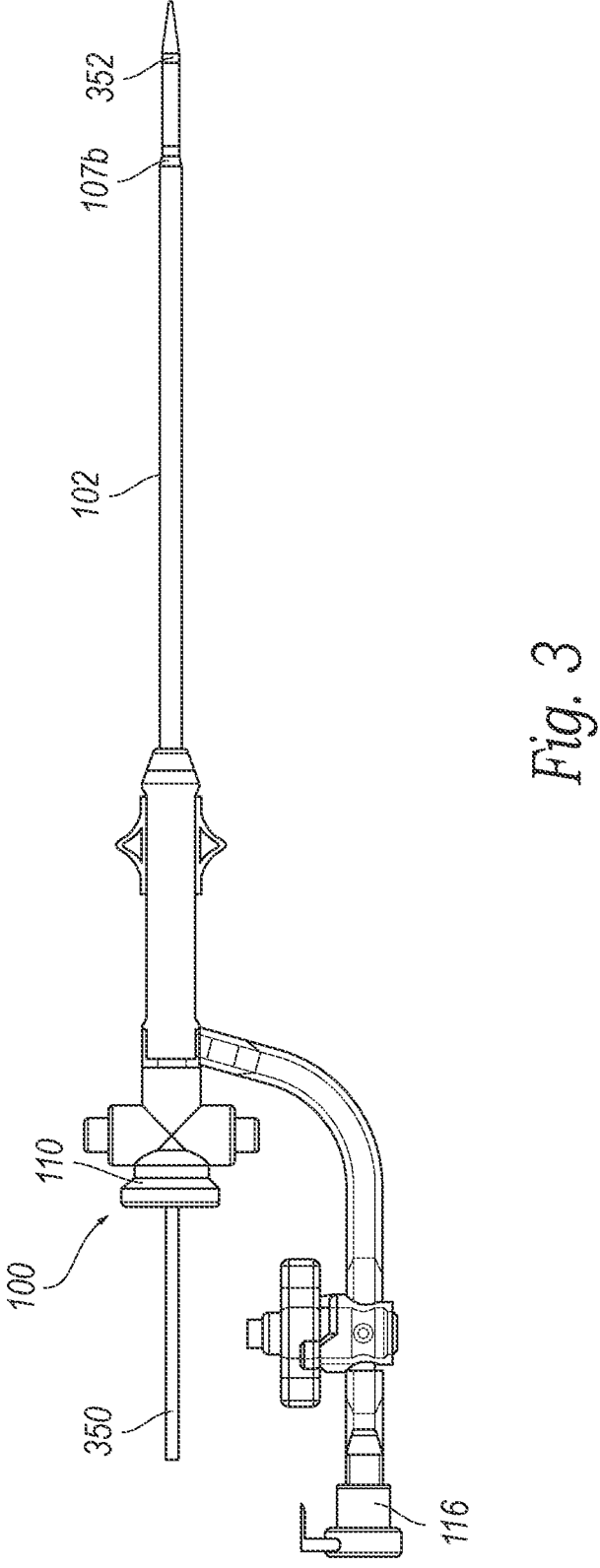
FIG. 3 is a side view of the funnel catheter assembly in the first position with a dilator inserted therethrough in accordance with embodiments of the present technology.

In some embodiments, the inner shaft 104 is sized to slidably receive one or more medical instruments inserted through the sealable hub 110 during an intravascular procedure using the funnel catheter assembly 100, such as a thrombectomy procedure. FIG. 3, for example, is a side view of the funnel catheter assembly 100 in the first position with a dilator 350 inserted through the sealable hub 110 and the lumen 108 of the inner shaft 104 (FIG. 1) in accordance with embodiments of the present technology. The dilator 350 can extend entirely through the inner shaft 104 and past the distal terminus of the distal portion 107*b* of the outer shaft 102 such that a distal tip 352 (e.g., an atraumatic tip) is positioned beyond the distal terminus of the outer shaft 102.

In some embodiments, the dilator 350 and the funnel catheter assembly 100 together define an introducer assembly that can be inserted into a patient (e.g., a human patient) and subsequently used to introduce intravascular medical devices into the patient. For example, the dilator 350 and the funnel catheter assembly 100 can be inserted into and advanced together through a blood vessel of the patient to a target location in the blood vessel. The dilator 350 can then be retracted proximally through the funnel catheter assembly 100, and the funnel catheter assembly 100 can be moved to the second position to expand the funnel 120 at the target location.

Referring to FIGS. 1-3 together, in one aspect of the present technology the inner shaft 104 is the "working" shaft of the funnel catheter assembly 100 that can be aspirated and/or receive various medical components (e.g., the dilator 350). In contrast, the outer shaft 102 is used to compress/expand the funnel 120. Accordingly, the shafts 102, 104 can be sized to maximize the size of the inner shaft 104 to permit larger-sized components to be inserted therethrough, or to provide greater aspiration force/power. For example, the outer shaft 102 can have an inner diameter that is only slightly greater than an outer diameter of the inner shaft 104. In some embodiments, the inner shaft 104 can have an outer diameter of at least 10 French, at least 12 French, at least 14 French, at least 18 French, at least 20 French, at least 22 French, at least 26 French, greater than 26 French, between 10 French and 26 French, between 14 French and 24 French, between 15 French and 21 French, between 16 French and 22 French, and/or any other or intermediate size. In some embodiments, the lumen 108 of the inner shaft 104 can have an internal diameter of at least 2 French, at least 10 French, at least 14 French, at least 18 French, at least 20 French, at least 22 French, between 11 French and 12 French, between 10 French and 22 French, between 14 French and 21 French, between 16 French and 20 French, and/or any other or intermediate size.

In another aspect of the present technology, the control assembly 130 is operable, via the movement of the actuation member 134 from the second position to the first position, to compress the funnel 120 after it has been expanded within a blood vessel. This can permit the funnel catheter assembly 100 to be repositioned within the blood vessel without fully withdrawing the funnel catheter assembly 100 from the patient. For example, after (i) introducing the funnel catheter assembly 100 into the blood vessel with the dilator 350 and (ii) removing the dilator 350, the funnel catheter assembly 100 can be repositioned proximally simply by moving the funnel catheter assembly 100 back to the first position to collapse the funnel 120 and then retracting the funnel catheter assembly 100 proximally. To reposition the funnel catheter assembly 100 distally, the dilator 350 can be reinserted and the funnel catheter assembly 100 pushed proximally in the first position with the funnel 120 compressed. Similarly, the funnel catheter assembly 100 can be fully withdrawn from the patient (e.g., at the conclusion of a thrombectomy procedure) in the first position with the funnel 120 compressed in the lumen 106 of outer shaft 102. Thus, the funnel catheter assembly 100 is configured to inhibit or even prevent the funnel 120 from contacting the wall of the blood vessel during advancement/withdrawal. This can help inhibit injury/damage to the patient that could otherwise be caused by the moving the funnel 120 through the blood vessel or an associated organ in the expanded state.

In some embodiments, the funnel catheter assembly 100 and/or methods of operating the funnel catheter assembly 100 can include some features the same as or similar to the thrombectomy systems (e.g., the introducer assemblies) described in detail in (i) U.S. Pat. No. 9,700,332, filed Sep. 16, 2016, and titled "INTRAVASCULAR TREATMENT OF VASCULAR OCCLUSION AND ASSOCIATED DEVICES, SYSTEMS, AND METHODS," and/or (ii) U.S. Pat. No. 10,098,651, filed Apr. 26, 2017, and titled "DEVICES AND METHODS FOR TREATING VASCULAR OCCLUSION," both of which are incorporated herein by reference in their entirety.

In other embodiments, the control assembly 130 can be configured to drive the distal and proximal movement of the outer shaft 102 in other manners. For example, the actuation member 134 can comprise a rotatable member (e.g., a ring gear, corkscrew, rotatable handle, etc.) coupled to the outer shaft 102. In some embodiments, the rotatable member can be a ratcheting member that is rotatable to a plurality of discreet positions between the first and second positions.

Similarly, in other embodiments the control assembly 130 can be operably coupled to the inner shaft 104 rather than the outer shaft 102. Accordingly, operation of the control assembly 130 can move the inner shaft 104 and the sealable hub 110 relative to the outer shaft 102 to move the funnel catheter assembly 100 between the first and second positions to constrain/compress and release/expand the funnel 120, respectively.

Figure 4:
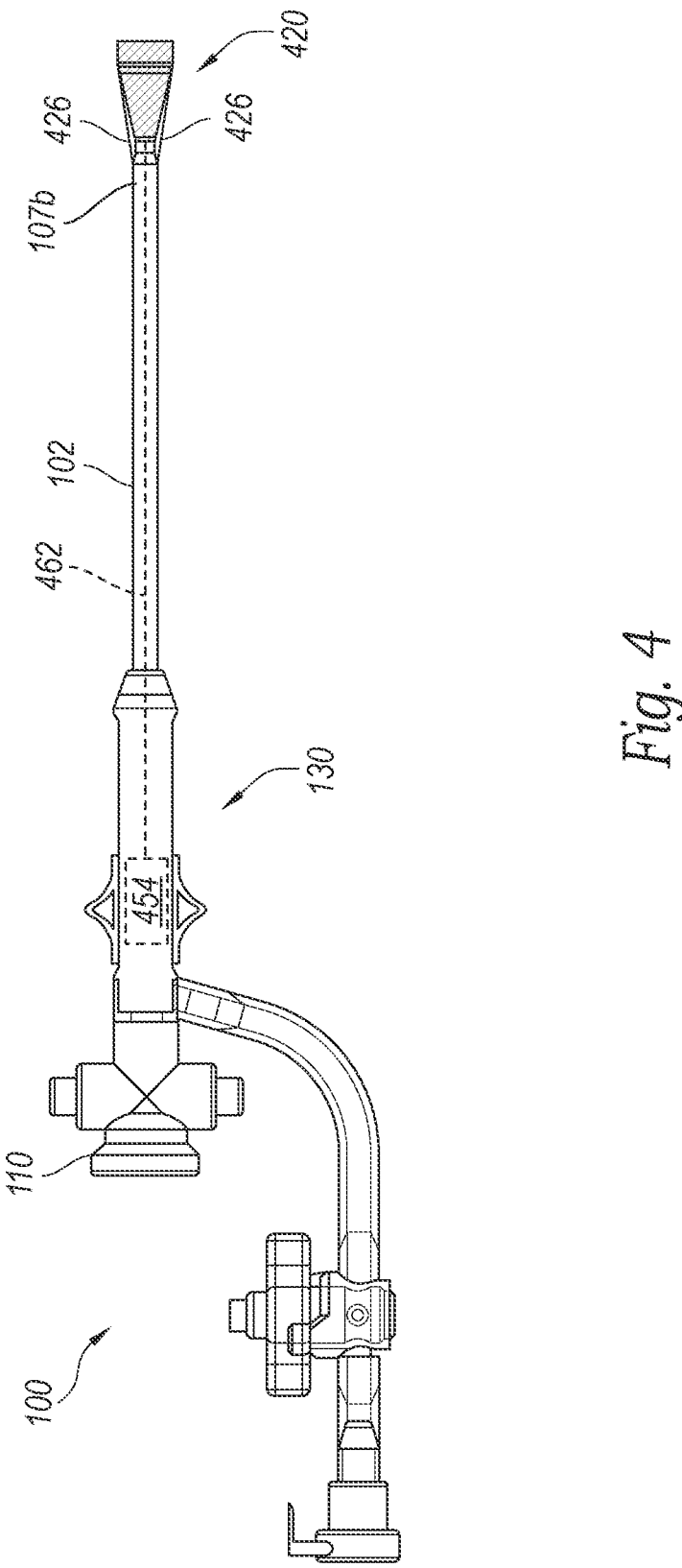
FIG. 4 is a side view of the funnel catheter assembly including a non-self-expanding funnel in accordance with embodiments of the present technology.

In yet other embodiments, the funnel 120 can be operably coupled to the outer shaft 102 such that movement of the outer shaft 102 between the first and second positions expands the funnel 120. More specifically, for example, FIG. 4 is a side view of the funnel catheter assembly 100 including a non-self-expanding funnel 420 in accordance with embodiments of the present technology. In some embodiments, the funnel 420 can have a similar shape as the funnel 120 described in detail above with reference to FIGS. 1-3, but can be formed of one or more non-self-expanding materials such as metal (e.g., a non-heat-activated metal), plastic, fiber, polymer, etc. In the illustrated embodiment, the funnel 420 is coupled to (i) the distal portion 109*b* of the inner shaft 104 (FIG. 1) and (ii) the distal portion 107*b* of the outer shaft 102 via a plurality of flexible tethers 426. The tethers 426 are configured (e.g., shaped, sized, and/or positioned) such that movement of the control assembly 130 from the first position to the second position pulls the tethers 426 to thereby pull and expand the funnel 420 as it is unsheathed from within the outer shaft 102.

In some embodiments, the funnel catheter assembly 100 can include one or more features for actuating/manipulating the funnel 420 (or the funnel 120 described in detail with reference to FIGS. 1-3). For example, the control assembly 130 can include an actuation member 454 (shown schematically) operably coupled to the funnel 420 via one or more control lines 462 (e.g., wires, tethers, rigid members etc.). The actuation member 454 can be a slider, rotatable member, or other component configured to exert a force on the funnel 420 via the control lines 462. In some embodiments, the control lines 462 can be asymmetrically/eccentrically coupled to the funnel 420 such that actuation of the actuation member 454 bends the funnel 420 away from a longitudinal axis of the shafts 102,104. In one aspect of the present technology, this arrangement can be used to help steer the funnel 420 into a tortuous region of a patient (e.g., a tortuous vessel, the left atrial appendage (LAA), etc.) that may otherwise be difficult to position the funnel 420 in. Additionally or alternatively, the funnel catheter assembly 100 can include one or more components (e.g., pull wires) for steering (e.g., bending, deflecting, etc.) the outer shaft 102 and/or the inner shaft 104 to facilitate positioning of the funnel 420.

II. SELECTED EMBODIMENTS OF PROCEDURES UTILIZING FUNNEL CATHETER ASSEMBLIES FOR EMBOLIC PROTECTION

Referring to FIGS. 1-4 together, the funnel catheter assembly 100 can be used in a myriad of procedures to capture thrombi and inhibit the thrombi from embolizing in portions of a patient's vasculature. For example, FIGS. 5-8 are schematic views illustrating various thrombectomy techniques for removing a thrombus T from a blood vessel BV of a human patient utilizing the funnel catheter assembly 100 in accordance with various embodiments of the present technology.

Figure 5:
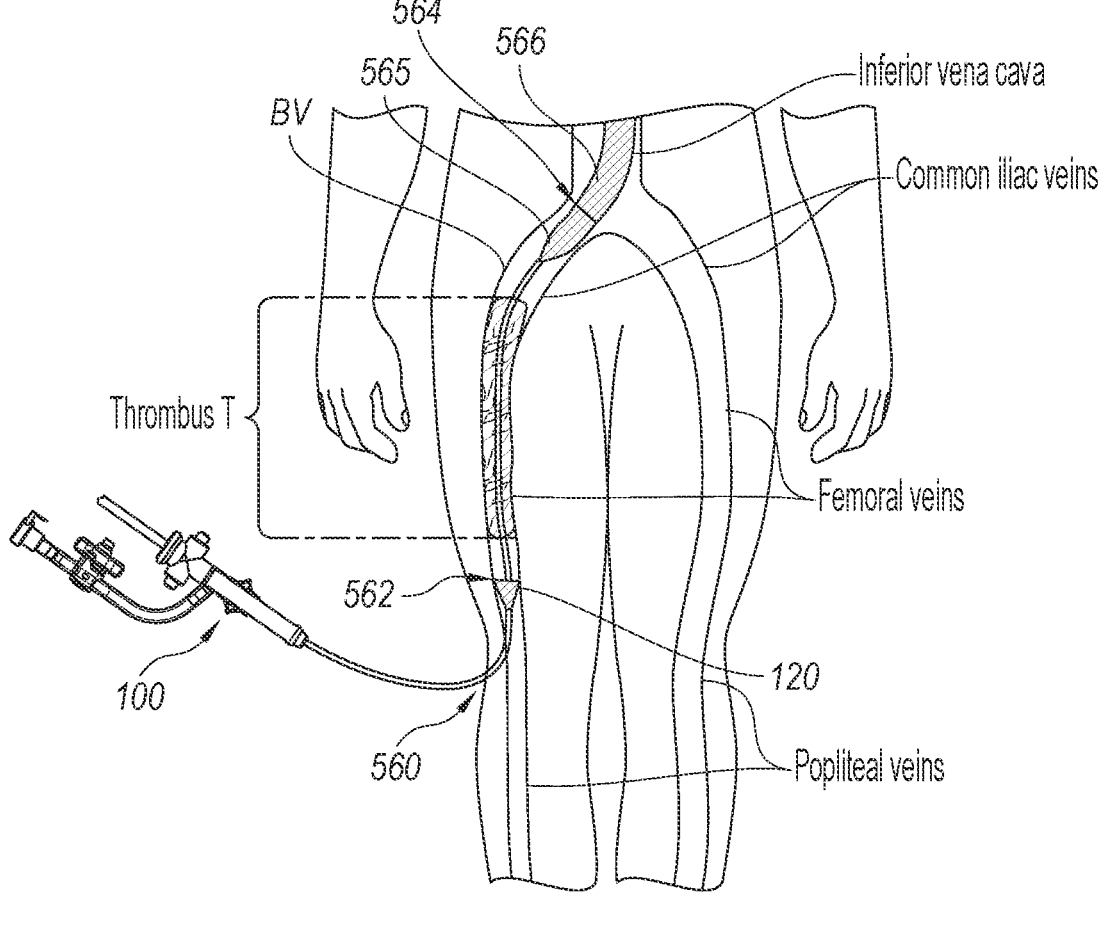
FIGS. 5-8 are schematic views illustrating various thrombectomy techniques for removing a thrombus from a blood vessel of a human patient utilizing the funnel catheter assembly in accordance with embodiments of the present technology.

Referring first to FIG. 5, in some embodiments the thrombus T (e.g., clot material) can be accessed through a popliteal access site 560. The funnel catheter assembly 100 can extend from the popliteal access site 560 to a deployment position 562 in the blood vessel BV at which the funnel 120 (or the funnel 420) can be deployed. The deployment position 562 can be proximate to and proximal of the thrombus T. The funnel 120 can at least partially appose a wall of the blood vessel BV after the funnel catheter assembly 100 is moved from the first position to the second position to expand the funnel 120, as described in detail above with reference to FIGS. 1-4.

In the illustrated embodiment, a thrombus extraction device 564 has been (i) inserted through the funnel catheter assembly 100, (ii) passed through the thrombus T in the direction of blood flow, and (iii) expanded distal of the thrombus T. The thrombus extraction device 564 can include a coring element 565 (e.g., a stent-like device) and a capture element 566 (e.g., a braided mesh bag). In some embodiments, some or all of the thrombus extraction device 564 can extend into one of the iliac veins and/or the inferior vena cava. After expansion distal of the thrombus T, the thrombus extraction device 564 can be retracted through the thrombus T and into the lumen 108 of the inner shaft 104 (FIG. 1) through the funnel 120. During retraction, the coring element 565 can core/separate the thrombus T and the capture element 566 can capture all or a portion of the thrombus T. In some embodiments, the thrombus extraction device 564 and the associated thrombectomy procedure can be generally similar or identical to the thrombus extraction devices and associated methods described in detail in (i) U.S. Pat. No. 9,700,332, filed Sep. 16, 2016, and titled "INTRAVASCULAR TREATMENT OF VASCULAR OCCLUSION AND ASSOCIATED DEVICES, SYSTEMS, AND METHODS," and/or (ii) U.S. Pat. No. 10,098,651, filed Apr. 26, 2017, and titled "DEVICES AND METHODS FOR TREATING VASCULAR OCCLUSION," both of which are incorporated herein by reference in their entirety.

In one aspect of the present technology, as the thrombus extraction device 564 and the captured thrombus T are retracted through the funnel 120, the funnel 120 can capture/retain any of the thrombus T that breaks free of the thrombus extraction device 564 as the thrombus extraction device 564 is compressed into the inner shaft 104. Accordingly, the funnel 120 can inhibit portions of the thrombus T from traveling upstream where they could potentially embolize. In some embodiments, a vacuum (e.g., a pre-charged vacuum) can be applied to the inner shaft 104 (e.g., via a syringe coupled to the syringe connector 116 shown in FIG. 1) at any point during retraction of the thrombus extraction device 564. In some embodiments, application of the vacuum can generate instantaneous or nearly instantaneous suction at the distal portion 109b of the inner shaft 104 that can aspirate any remaining portions of the thrombus T into and/or through the inner shaft 104.

Figure 6:
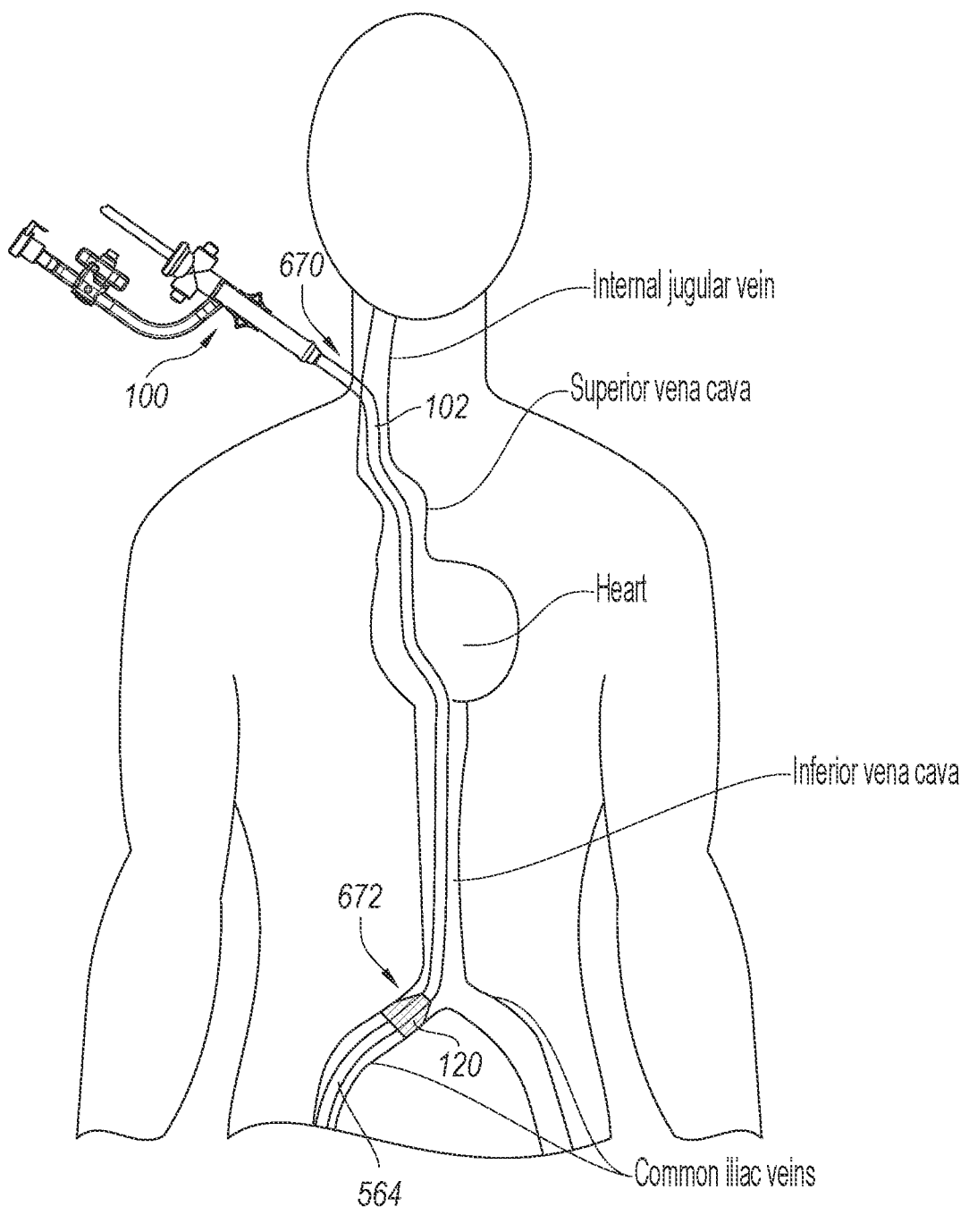

Referring next to FIG. 6, in some embodiments the thrombus T (not shown in FIG. 6; e.g., positioned lower in the iliac or femoral veins) can be accessed through an internal jugular access site 670, and the funnel catheter assembly 100 can be inserted into the patient's body via the internal jugular access site 670. The funnel catheter assembly 100 can extend from the internal jugular access site 670 to a deployment position 672 at which the funnel 120 (or the funnel 420) can be deployed proximal to the thrombus T. In the illustrated embodiment, the outer shaft 102 and the inner shaft 104 (obscured in FIG. 6) extend from the internal jugular access site 670 through the superior vena cava and the inferior vena cava to the deployment position 672 in one of the common iliac veins. In some embodiments, the deployment position 672 can be located in, for example, the inferior vena cava, one of the iliac veins, the femoral vein, the popliteal vein, before or beyond the iliac arch, or any other location proximate to and/or proximal to the thrombus T. In some embodiments, the thrombus extraction device 564 can be inserted through the funnel catheter assembly 100 and withdrawn through the thrombus T to capture the thrombus T, as described in detail above with reference to FIG. 5.

In one aspect of the present technology, accessing the thrombus T via the internal jugular access site 670 allows the funnel 120 to be positioned downstream of the thrombus T. Accordingly, the funnel 120 can capture any of the thrombus T that may break off and be carried downstream toward the heart during operation of the thrombus extraction device 564. In another aspect of the present technology, the funnel 120 can be compressed—for example, by moving the actuation member 134 from the second position to the first position as described in detail above with reference to FIGS. 1-4—before withdrawing the funnel catheter assembly 100 at the conclusion of the thrombectomy procedure. This prevents the funnel 120 from being withdrawn in the expanded configuration through the heart of the patient (e.g., through the right atrium) which could potentially damage the heart.

Figure 7:
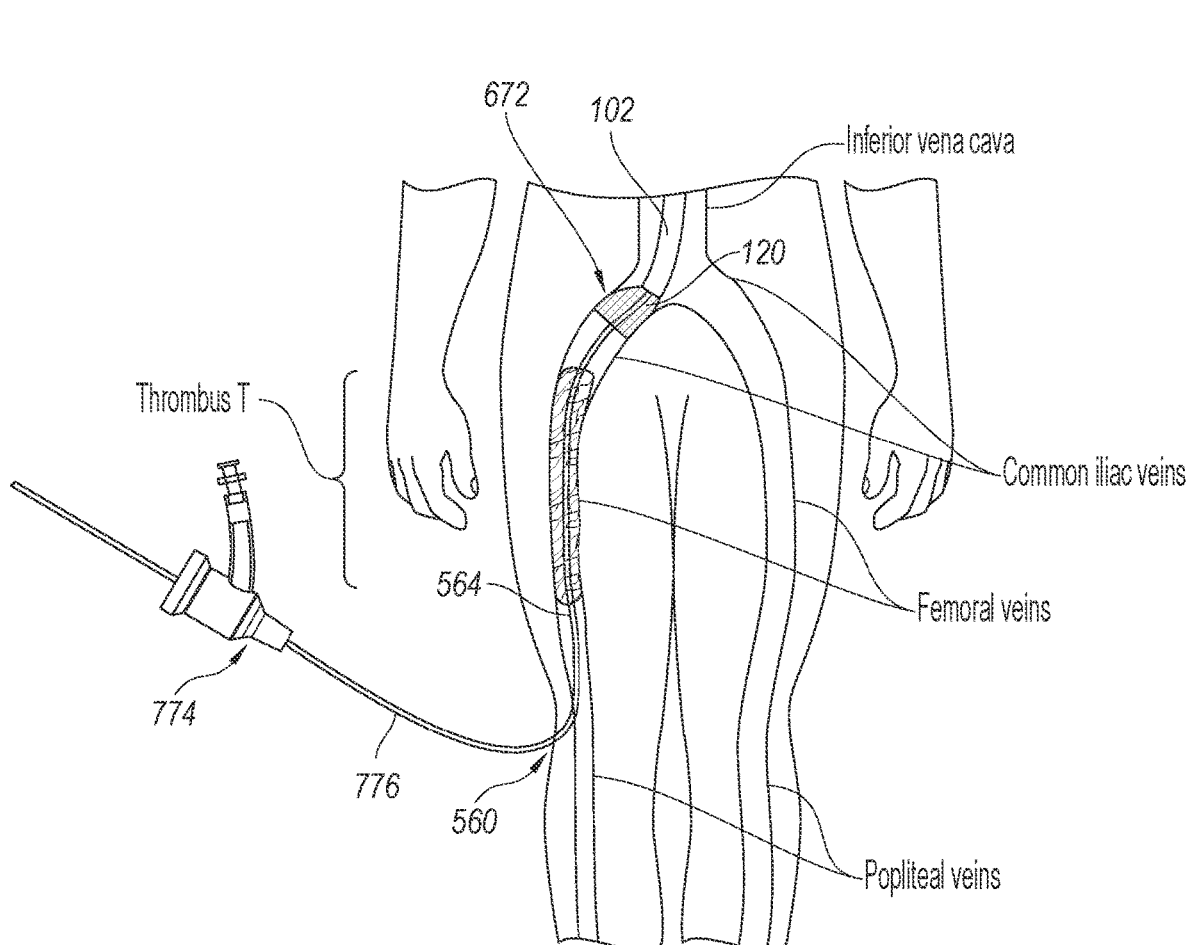

Referring next to FIG. 7, in some embodiments the thrombus T can be accessed by the thrombus extraction device 564 through the popliteal access site 560 using a separate introducer assembly 774, while the funnel catheter assembly 100 can be inserted into the patient's body via the internal jugular access site 670 (FIG. 6). The funnel 120 can be expanded at the deployment position 672 during a thrombectomy procedure using the thrombus extraction device 564. The funnel 120 can therefore capture any of the thrombus material T that may break away and flow downstream during the procedure. In the illustrated embodiment, the thrombus extraction device 564 is inserted through an outer shaft 776 of the introducer assembly 774. In one aspect of the present technology, in comparison to using the funnel catheter assembly 100 as the introducer for the thrombus extraction device 564, the outer shaft 776 can be made relatively larger than the inner shaft 104 because the outer shaft 102 need not be positioned thereabout for constraining the funnel 120. This can permit the thrombus extraction device 564 to be made larger and/or enable greater aspiration forces to be generated through the outer shaft 776.

Figure 8:
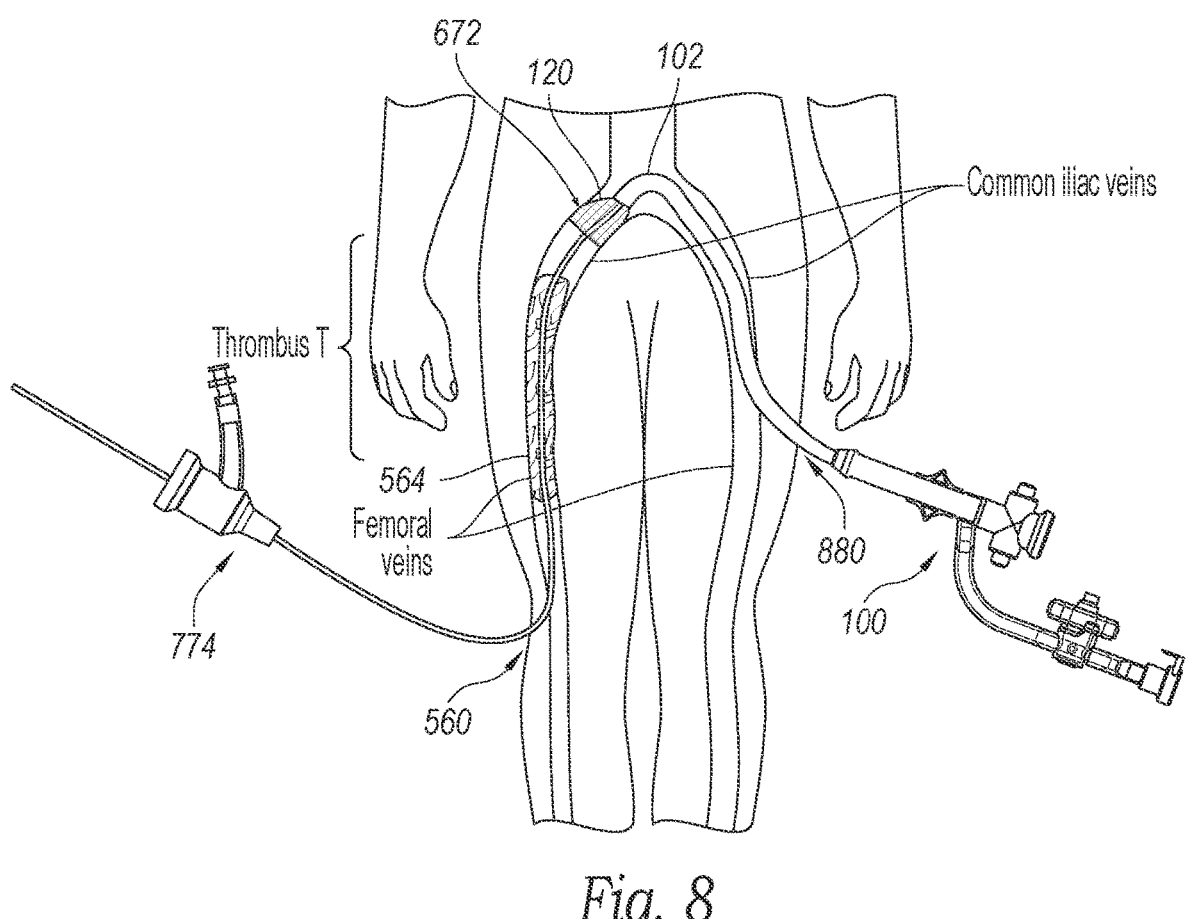

Referring next to FIG. 8, in some embodiments the thrombus T can be accessed by the thrombus extraction device 564 through the popliteal access site 560 using the introducer assembly 774, while the funnel catheter assembly 100 can be inserted into the patient's body via a femoral access site 880. The funnel catheter assembly 100 can traverse the common iliac veins to the deployment position 672, or another suitable deployment position.

In other embodiments, the funnel catheter assembly 100 can be inserted into a patient's body via other venous or arterial access sites, and can be used in a myriad of different procedures. For example, additional applications of the funnel catheter assembly 100 include but are not limited to:

Internal jugular vein (IJ) access for deployment in the inferior vena cava (IVC) for treatment of lower extremity deep vein thrombsis (DVT);

IJ access for deployment in the IVC for removal of IVC filters and/or treatment of thrombus located in the IVC;

IJ access for deployment in the deep veins of the lower extremity veins (iliac, femoral, popliteal veins, etc.) for treatment of lower extremity DVT;

Common femoral vein (CFV) access for deployment in the superior vena cava (SVC) for treatment of upper extremity DVT and/or SVC thrombus;

CFV access for deployment in the upper extremity veins (brachiocephalic, subclavian, axillary veins, etc.) for treatment of upper extremity DVT and/or SVC thrombus;

CFV access for deployment in the pulmonary arteries (PAs) for treatment of pulmonary embolism;

CFV access with transseptal access for deployment in the left atrium ostium and the left atrial appendage (LAA) for thrombus removal;

Internal Carotid Artery (ICA) access for deployment in the common carotid artery (CCA) for carotid endarterectomy (CEA);

ICA access for deployment in descending thoracic aorta for treatment of thoraco-abdominal and/or abdominal aortic (AA) thrombus and/or aorto-arterial thrombosis;

ICA access for deployment in the descending/thoracic aorta for treatment of renal thrombosis;

ICA access for intra-arterial placement for treatment of superior mesenteric artery (SMA) thrombosis (MAT);

Common Femoral Artery (CFA) access for treatment of atherosclerosis in the brachial artery, radial artery, popiteal artery, or dorsalis pedis artery;

CFA access for deployment in the common iliac artery for treatment of aorto-arterial thrombosis and/or occlusions;

CFA access for deployment in the abdominal aorta for treatment of renal artery thrombosis; and/or CFA access for deployment in the aorta for treatment of thoraco-abdominal and/or AA thrombus and/or aorto-arterial thrombosis.

Figure 9A:
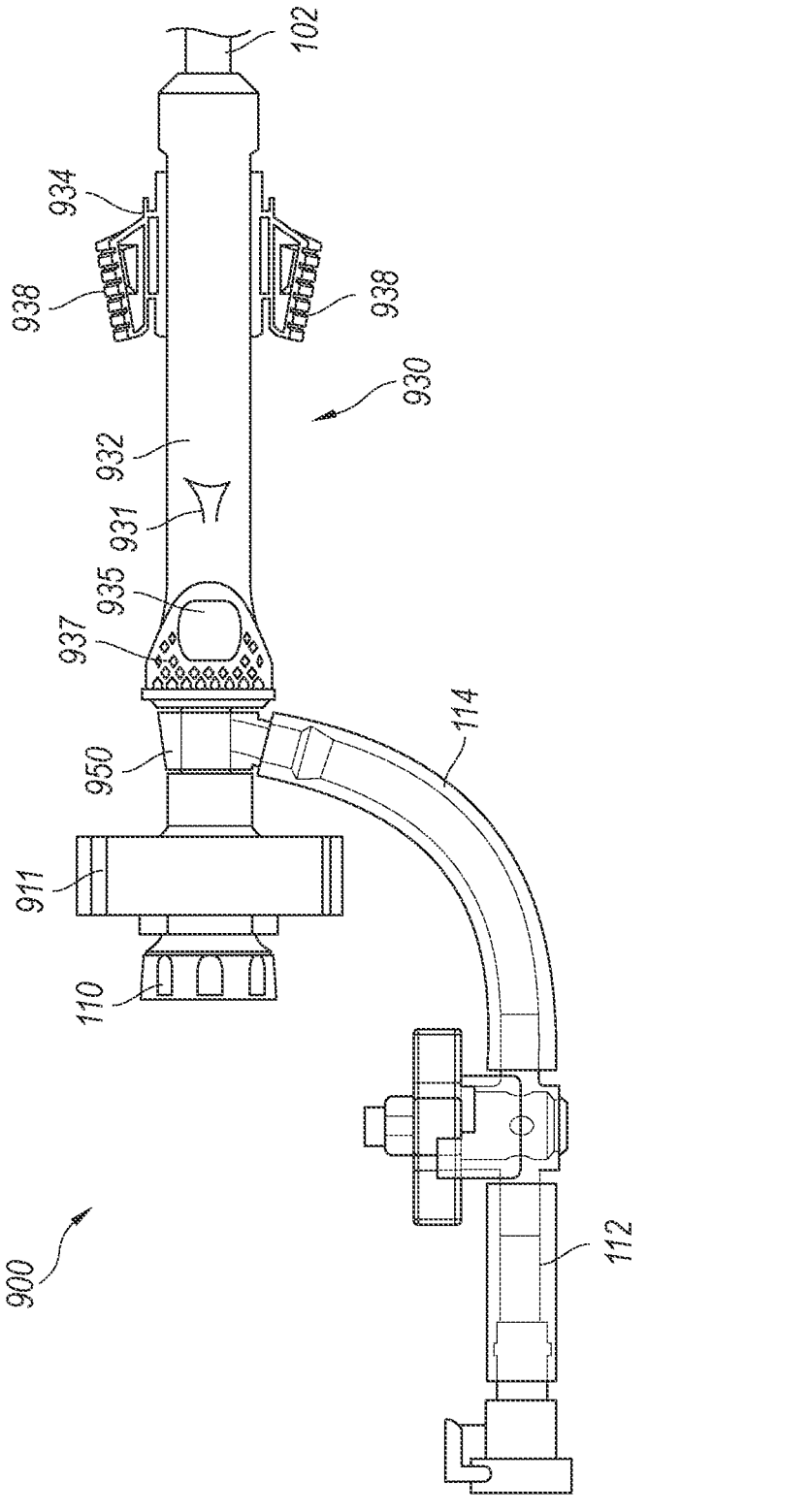
FIGS. 9A-9C are enlarged, partially transparent side and side cross-sectional views, respectively, of a portion of a funnel catheter assembly in accordance with additional embodiments of the present technology.
Figure 9B:
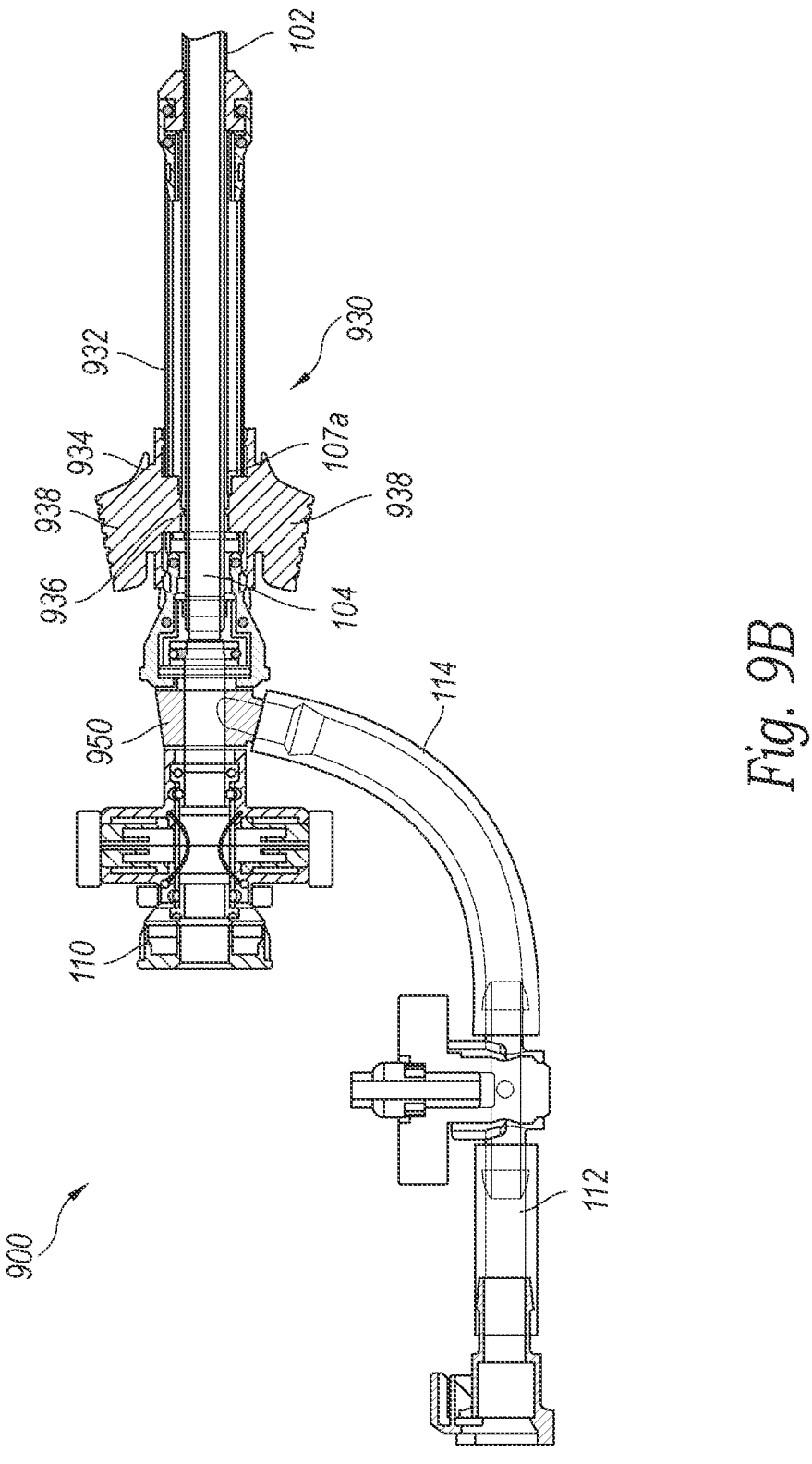

FIGS. 9A and 9B are enlarged, partially transparent side and side cross-sectional views, respectively, of a portion of a funnel catheter assembly 900 in accordance with additional embodiments of the present technology. Referring to FIGS. 9A and 9B together, the funnel catheter assembly 900 can include some features that are at least generally similar in structure and function, or identical in structure and function, to the corresponding features of the funnel catheter assembly 100 described in detail above with reference to FIGS. 1-8, and can operate in a generally similar or identical manner to the funnel catheter assembly 100. In the illustrated embodiment, for example, the funnel catheter assembly 900 includes the sealable hub 110, the connecting tube

114, the aspiration port 112, the outer shaft 102, and the inner shaft 104 (obscured in FIG. 9A). The funnel catheter assembly 900 further includes a control assembly 930 including a housing 932 and an actuation member 934 having a pair of grip member 938. As shown in FIG. 9B, the actuation member 934 includes a hub 936 positioned within the housing 932 and coupled to the outer shaft 102 (e.g., the proximal portion 107a of the outer shaft 102). The actuation member 934 is movable (e.g., slidable) relative to the housing 932 to advance/retract the outer shaft 102 relative to the inner shaft 104 and a funnel (e.g., the funnel 120 shown in FIGS. 10B and 10C) attached to a distal portion thereof.

The funnel catheter assembly 900 is in a first, sheathed position in FIG. 9A in which the funnel is constrained by the outer shaft 102 and in a second, unsheathed position in FIG. 9B in which the funnel is not constrained by the outer shaft 102. Referring to FIG. 9A, in some embodiments the housing 932 can include a marking 931 indicating a position of the actuation member 934 in which the funnel is in the unsheathed position. In some embodiments, a proximal portion 933a of the housing 932 can include gripping features, such as a groove 935, a cross-hatched pattern 937, and/or other features for increasing the grip-ability of the housing 932. In some embodiments, an operator can grip the housing 932 (e.g., via the groove 935 and/or the pattern 937) while moving (i) the actuation member 934 relative to the housing 932 and/or (ii) the housing 932 relative to the actuation member 934. In some embodiments, the funnel catheter assembly 900 can further include a lock mechanism 911 that can be attached to the sealable hub 110 (e.g., to buttons thereof) to lock the sealable hub 110 in the open/unsealed position.

Figure 9C:
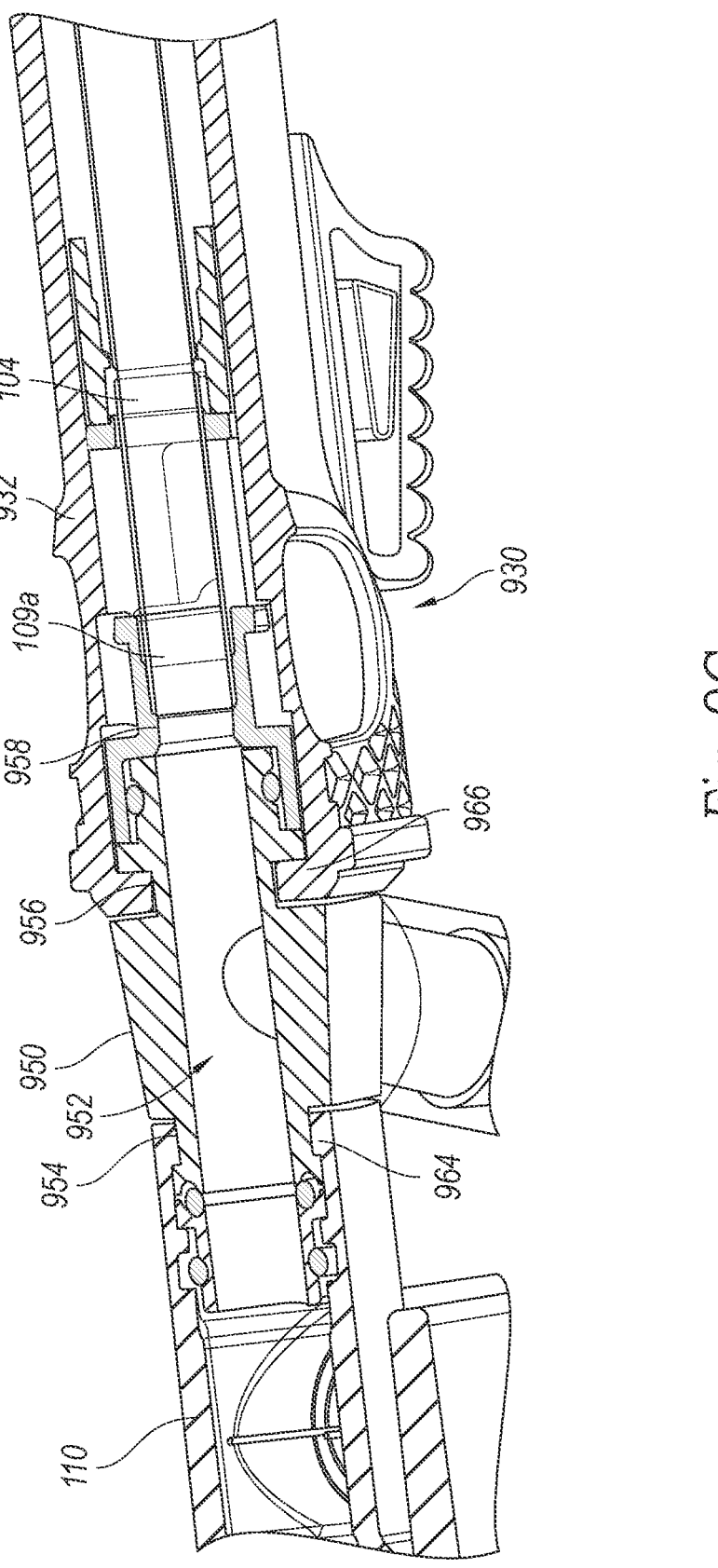

In the illustrated embodiment, the funnel catheter assembly 900 further includes a rotatable side port 950 fluidly connecting the sealable hub 110, the connecting tube 114, and the inner shaft 104. FIG. 9C is an enlarged isometric cross-sectional view of a portion of the sealable hub 110, the rotatable side port 950, and the control assembly 930 in accordance with embodiments of the present technology. Referring to FIG. 9C, the side port 950 defines a lumen 952 that provides a fluid path from the inner shaft 104 to the sealable hub 110. In the illustrated embodiment, the side port 950 includes a first groove 954 and a second groove 956 that each extend circumferentially about an outer surface of the side port 950. The sealable hub 110 includes a first projection 964 positioned in the first groove 954 and the housing 932 includes a second projection 966 positioned in the second groove 956. The engagement of the first and second projections 964, 966 in the first and second grooves 954, 956 couples the housing 932 to the sealable hub 110. Moreover, the first and second projections 964, 966 are rotatable within the first and second grooves 954, 956 such that the sealable hub 110, the side port 114, and the housing 932 can each rotate independently of one another while remaining coupled together.

In some embodiments, the control assembly 930 can further include a connector 958 coupled to the proximal portion 109a of the inner shaft 104 and positioned at least partially between the side port 950 and the housing 932. The connector 958 can be rotatable within the housing 932 such that the housing 932 can rotate independently of the connector 958 and the inner shaft 104. Accordingly, in some aspects of the present technology rotation of the sealable hub 110, the side port 950 (e.g., the aspiration port 112 shown in FIGS. 9B and 9C), and/or the housing 932 will not substantially rotate the inner shaft 104. This can help inhibit the funnel attached to the inner shaft 104 from rotating within a vessel during a procedure using the funnel catheter assembly 900—while still allowing for movement of the sealable hub 110, the side port 950, and/or other components of the funnel catheter assembly 900.

Figures 10A, 10B, 10C:
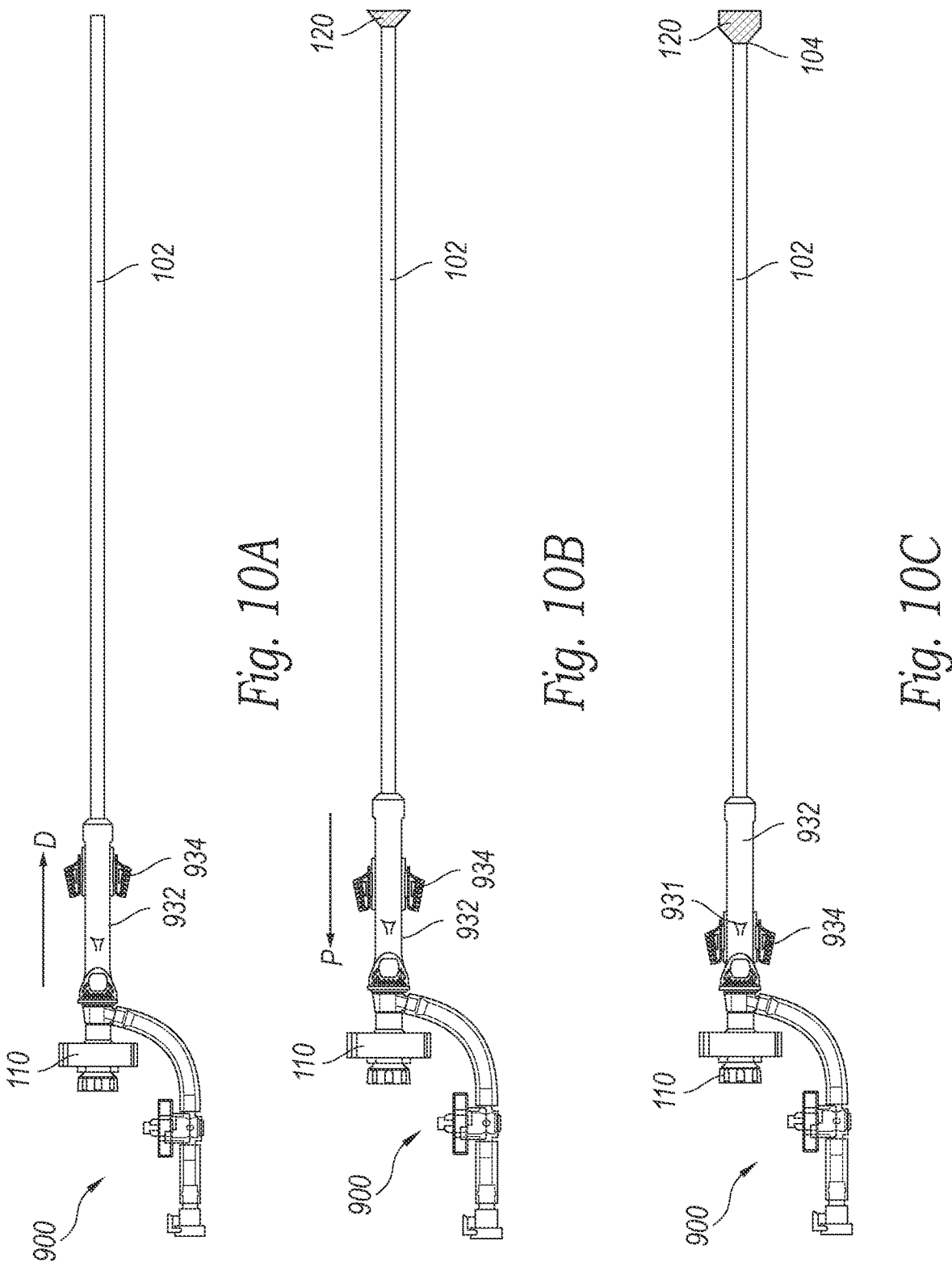
FIGS. 10A-10C are side views of the funnel catheter assembly of FIGS. 9A and 9B in a sheathed position, a partially-unsheathed or intermediate position, and an unsheathed position, respectively, in accordance with embodiments of the present technology.

FIGS. 10A-10C are side views of the funnel catheter assembly 900 in the sheathed position, a partially-un-sheathed or intermediate position, and the unsheathed position, respectively, in accordance with embodiments of the present technology. Referring to FIGS. 10A-10C together, the funnel catheter assembly 900 can be moved between the sheathed and unsheathed positions by moving the actuation member 934 relative to the housing 932 and/or by moving the housing 932 (and the coupled sealable hub 110) relative to the actuation member 934. In some embodiments, for example, the operator can slide the actuation member 134 relative to the housing 932 in the direction indicated by the arrow P in FIG. 10B to retract the outer shaft 102 to unsheathe the funnel 120. In some aspects of the present technology, moving the actuation member 934 rather than the housing 932 moves only the outer shaft 102 such that the funnel 120 remains in a constant or generally constant position (e.g., stationary position). In other embodiments, the operator can advance the housing 932 relative to the actuation member 934 in the direction indicated by the arrow D in FIG. 10A to unsheathe the funnel 120. In some aspects of the present technology, moving the housing 932 relative to the actuation member 934 advances the inner shaft 104 and the funnel 120 distally relative to the outer shaft 102.

In the unsheathed position shown in FIG. 10C, the actuation member 934 can be positioned adjacent or near the marking 931 to indicate to the operator that the funnel 120 is deployed. In some embodiments, to re-sheathe the funnel 120 (e.g., from the unsheathed position shown in FIG. 10C to the sheathed position shown in FIG. 10A), the operator can retract the housing 932 relative to the actuation member 934 (e.g., in the direction of the arrow P) to pull the funnel 120 into the outer shaft 102. In some aspects of the present technology, such a retracting motion can be intuitive to the user as the motion of the housing 932 is in the same direction as the removal/collapse of the funnel 120. Nevertheless, in other embodiments the operator can advance the actuation member 934 relative to the housing 932 to sheathe the funnel 120 within the outer shaft 102.

FIG. 11 is a flow diagram of a process or method 1110 for operating the funnel catheter assembly 100 and/or the funnel catheter assembly 900 (collectively referred to as "the funnel catheter assembly") during an intravascular procedure in accordance with embodiments of the present technology. Although some features of the method 1110 are described in the context of the embodiments shown in FIGS. 1-10C for the sake of illustration, one skilled in the art will readily understand that the method 1110 can be carried out using other suitable systems and/or devices described herein.

At block 1111, the method 1110 includes inserting the funnel catheter assembly into a patient's body via a vascular site. For example, the dilator 350, the outer shaft 102, and inner shaft 104 can be inserted together through a venous or arterial access site.

At block 1112, the method 1110 includes advancing the funnel catheter assembly to a deployment position within the vasculature of the patient. For example, the dilator 350, the outer shaft 102, and inner shaft 104 can be advanced together through the vasculature to the selected deployment position. The funnel catheter assembly can be advanced in the first position such that the funnel 120 is constrained/compressed within the outer shaft 102. The deployment position can be a portion of a blood vessel, a portion of the heart, or another suitable location.

At block 1113, the method 1110 includes expanding the funnel 120 at the deployment position. For example, the control assembly 130 of the funnel catheter assembly 100 can be moved from the first position to the second position to release/unsheathe the funnel 120 from within the outer shaft 102, thereby allowing the funnel 120 to expand at the deployment position. Likewise, the actuation member 934 can be slid relative to the housing 932 to unsheathe the funnel 120. After expansion, the funnel 120 can appose/contact the anatomy surrounding the deployment position, such as a wall of a blood vessel. In some embodiments, the dilator 350 can be removed from the funnel catheter assembly before expanding the funnel 120.

At block 1114, the method 1110 optionally includes compressing and repositioning the funnel 120. For example, the control assembly 130 can be moved from the second position to the first position to constrain/sheathe the funnel 120 within the outer shaft 102. Likewise, the housing 932 of the funnel catheter assembly 900 can be retracted proximally relative to the actuation member (and/or the actuation member 934 can be advanced distally relative to the housing) to sheathe the funnel 120. Then, the funnel catheter assembly can be repositioned to a different deployment position (block 1112) and expanded once again (block 1113). In some embodiments, the dilator 350 can be reinserted into the funnel catheter assembly 100 before repositioning the funnel catheter assembly 100.

At block 1115, the method 1110 includes maintaining the funnel 120 in the expanded position during an intravascular procedure. As described in detail above, the funnel 120 can capture thrombi that break free during the intravascular procedure to inhibit their embolization elsewhere in the vasculature of the patient.

At block 1116, the method 1110 includes compressing the funnel 120 and withdrawing the funnel catheter assembly 100 from the patient. For example, the control assembly 130 of the funnel catheter assembly 100 can be moved from the second position to the first position to constrain/sheathe the funnel 120 within the outer shaft 102, and the funnel catheter assembly 100 can then be withdrawn proximally to and from the vascular access site. Likewise, the housing 932 of the funnel catheter assembly 900 can be retracted proximally relative to the actuation member (and/or the actuation member 934 can be advanced distally relative to the housing) to sheathe the funnel 120.

III. EXAMPLES

Several aspects of the present technology are set forth in the following examples:

1. A funnel catheter assembly, comprising:
an outer shaft defining a lumen;
an inner shaft extending through the lumen and having a proximal portion and a distal portion;
an expandable funnel coupled to the distal portion of the inner shaft; and
a control assembly configured to move the funnel between a first position and a second position, wherein—
in the first position, the funnel is constrained within the lumen of the outer shaft, and
in the second position, the funnel is positioned at least partially outside the lumen of the outer shaft such that the funnel can expand.

2. The funnel catheter assembly of example 1 wherein the control assembly is coupled to the outer shaft and configured to move the outer shaft relative to the inner shaft.

3. The funnel catheter assembly of example 1 or example 2 wherein the control assembly includes an actuator movable to move the funnel between the first and second positions.

4. The funnel catheter assembly of example 3 wherein the actuator is a slider.

5. The funnel catheter assembly of any one of examples 2-4 wherein the funnel includes a proximal portion and a distal portion, and wherein the proximal portion of the funnel is coupled to the distal portion of the inner shaft.

6. The funnel catheter of example 5 wherein the distal portion of the funnel is coupled to the outer shaft.

7. The funnel catheter assembly of any one of examples 1-6, further comprising a sealable hub and a side port, wherein the side port is rotatably coupled between the control assembly and the sealable hub.

8. A funnel catheter assembly, comprising:

an outer shaft defining an outer lumen;

an inner shaft extending through the outer lumen and having a proximal portion and a distal portion;

an expandable funnel coupled to the distal portion of the inner shaft; and a control assembly operably coupled to the proximal portion of the outer shaft and configured to move the outer shaft between a first position and a second position, wherein— in the first position, the outer shaft is positioned at least partially over the funnel to radially constrain the funnel, and in the second position, the outer shaft is retracted proximally relative to the funnel such that the funnel can radially expand.

9. The funnel catheter assembly of example 8 wherein the control assembly includes a housing and an actuation member, wherein the actuation member is coupled to a proximal portion of the outer shaft, and wherein the actuation member is slidable along the housing to move the outer shaft between the first and second positions.

10. The funnel catheter assembly of example 8 or example 9 wherein the funnel is configured to self-expand.

11. The funnel catheter assembly of example 8 or example 9 wherein the funnel is non-self-expanding, wherein the funnel is further coupled to a distal portion of the outer shaft, and wherein movement of the outer shaft from the first position to the second position is configured to expand the funnel.

12. The funnel catheter assembly of example 11 wherein a distal portion of the funnel is coupled to the distal portion of the outer shaft via one or more tethers.

13. The funnel catheter assembly of any one of examples 8-12 wherein the inner shaft defines an inner lumen sized to receive a dilator.

14. A method of operating a funnel catheter assembly during an intravascular procedure on a patient, the method comprising:

at least partially inserting an inner shaft, an outer shaft, and a funnel of the funnel catheter assembly into the vasculature of the patient;

advancing the inner shaft, the outer shaft, and the funnel together to a deployment position within the vasculature of the patient, wherein the funnel is sheathed within a lumen of the outer shaft during the advancement;

moving the outer shaft relative to the inner shaft to unsheathe the funnel and permit the funnel to expand to an expanded position;

maintaining the funnel in the expanded position during at least a portion of the intravascular procedure;

moving the outer shaft relative to the inner shaft and/or moving the inner shaft relative to the outer shaft to sheath the funnel within the lumen of the outer shaft; and withdrawing the funnel catheter assembly from the patient.

15. The method of example 14 wherein the funnel is self-expandable, and wherein moving the outer shaft relative to the inner shaft to unsheathe the funnel includes permitting the funnel to self-expand to the expanded position.

16. The method of example 14 or example 15 wherein moving the outer shaft relative to the inner shaft to unsheathe the funnel includes moving a slider of a control assembly of the funnel catheter assembly from a first position to a second position, and wherein the slider is coupled to a proximal portion of the outer shaft.

17. The method of any one of examples 14-16 wherein moving the outer shaft relative to the inner shaft to unsheathe the funnel includes rotating a rotatable element of a control assembly of the funnel catheter assembly from a first position to a second position.

18. The method of any one of examples 14, 16, and 17 wherein the funnel is non-self-expanding, and wherein the method further comprises actuating the funnel to expand to the expanded position.

19. The method of any one of examples 14-18 wherein— inserting the inner shaft, the outer shaft, and the funnel into the vasculature of the patient further includes at least partially inserting a dilator positioned within the inner shaft into the vasculature of the patient; and advancing the inner shaft, the outer shaft, and the funnel further includes advancing the inner shaft, the outer shaft, the funnel, and the dilator together to the deployment position.

20. The method of any one of examples 14-19 wherein moving the outer shaft relative to the inner shaft to unsheathe the funnel includes moving the outer shaft in a first direction, and wherein the method further comprises moving the outer shaft relative to the inner shaft to sheath the funnel by moving the outer shaft in a second direction opposite to the first direction.

IV. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A funnel catheter assembly, comprising:

an outer shaft defining an outer lumen and having a proximal portion and a distal portion;

an inner shaft extending through the outer lumen and having a proximal portion and a distal end portion, wherein the inner shaft defines an inner lumen;

an expandable funnel coupled to the distal end portion of the inner shaft and extending distally from the distal end portion of the inner shaft;

a control assembly comprising (a) a housing having a proximal portion and a distal portion and defining a housing lumen and (b) an actuator movably coupled to the housing, wherein— the inner shaft extends at least partially through the housing lumen and is fixed in position longitudinally relative to the housing in a direction extending between the proximal portion and the distal portion of the housing, the proximal portion of the outer shaft is positioned at least partially within the housing lumen and operably coupled to the actuator, the actuator is configured to be actuated to move the proximal portion of the outer shaft at least partially through the housing lumen to move the funnel between a first position and a second position, in the first position, the funnel is constrained within the outer lumen of the outer shaft, and in the second position, the funnel is positioned at least partially outside the outer lumen of the outer shaft such that the funnel can expand to enclose a volume; and a side port coupled to the control assembly and having a proximal portion and a distal portion, wherein the distal portion of the side port is rotatably coupled to the proximal portion of the housing, wherein the side port defines a first lumen extending between the proximal portion of the side port and the distal portion of the side port and fluidly coupled to the inner lumen, wherein the side port includes a side port connector between the proximal portion of the side port and the distal portion of the side port and defining a second lumen branching from the first lumen and fluidly coupled to the inner lumen via the first lumen, and wherein the second lumen is configured to be fluidly coupled to a source of aspiration configured to aspirate the inner lumen to aspirate the volume of the funnel; and a hemostasis valve rotatably coupled to the proximal portion of the side port for rotational movement of the hemostasis valve relative to the side port, wherein the hemostasis valve is actuatable to selectively provide fluid access to the inner lumen and the first lumen.

2. The funnel catheter assembly of claim 1 wherein the actuator is fixedly coupled to the outer shaft and configured to slide the outer shaft relative to the inner shaft.

3. The funnel catheter assembly of claim 2 wherein the actuator is configured to be actuated to move the proximal portion of the outer shaft at least partially through the housing lumen proximally toward the proximal portion of the housing to move the funnel from the first position to the second position.

4. The funnel catheter assembly of claim 3 wherein the actuator comprises (a) a coupling portion positioned at least partially within the housing lumen and fixedly coupled to the proximal portion of the outer shaft and (b) a slider portion extending outside the housing lumen and configured to be grasped by a user and slid along the housing at least partially proximally toward the proximal portion of the housing to correspondingly move the coupling portion and the proximal portion of the outer shaft through the housing lumen to move the funnel from the first position to the second position.

5. The funnel catheter assembly of claim 1 wherein the funnel includes a proximal portion and a distal portion, and wherein the proximal portion of the funnel is coupled to the distal end portion of the inner shaft.

6. The funnel catheter of claim 5 wherein the distal portion of the funnel is coupled to the outer shaft.

7. The funnel catheter assembly of claim 1, further comprising a connector fixedly coupled to the proximal portion of the inner shaft, wherein the connector is rotatably coupled within the housing lumen.

8. The funnel catheter assembly of claim 7 wherein the side port, the hemostasis valve, and the housing are configured to rotate independently of the connector and the inner shaft.

9. The funnel catheter assembly of claim 1 further comprising:

aspiration tubing fluidly coupled to the branch-second lumen;

the aspiration source, wherein the aspiration source is fluidly coupled to the aspiration tubing; and a fluid control device fluidly coupled along the aspiration tubing, wherein the fluid control device is actuatable to selectively fluidly connect the aspiration source to the inner lumen via the first lumen and the second lumen.

10. The funnel catheter assembly of claim 1 wherein the proximal portion of the outer shaft is constrained to move through the housing lumen only between the proximal portion of the housing and the distal portion of the housing.

11. The funnel catheter assembly of claim 1 wherein the actuator is configured to slide proximally along the housing to move the proximal portion of the outer shaft proximally at least partially through the housing lumen to move the funnel between the first position and the second position.

12. The funnel catheter assembly of claim 1 wherein the side port further comprises:

a first groove at the distal portion of the side port; and a second groove at the proximal portion of the side port, wherein the first groove and the second groove extend circumferentially about an outer surface of the side port;

the hemostasis valve comprises a first projection positioned in the first groove; and the proximal portion of the housing further comprises a second projection positioned in the second groove.

13. The funnel catheter assembly of claim 12 wherein the first projection is constrained to rotate circumferentially within the first groove, and wherein the second projection is constrained to rotate circumferentially within the second groove.

14. The funnel catheter assembly of claim 12 wherein the hemostasis valve, the side port, and the housing can each freely rotate independently of one another while remaining coupled together.

* * * * *